United States Patent
Maki et al.

(10) Patent No.: US 7,359,825 B2
(45) Date of Patent: Apr. 15, 2008

(54) OPTICAL MEASUREMENT INSTRUMENT AND OPTICAL MEASUREMENT METHOD

(75) Inventors: Atsushi Maki, Hachioji (JP); Yuuichi Yamashita, Kawagoe (JP); Tsuyoshi Yamamoto, Hatoyama (JP); Hideaki Koizumi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 191 days.

(21) Appl. No.: 11/378,448

(22) Filed: Mar. 20, 2006

(65) Prior Publication Data

US 2006/0178839 A1    Aug. 10, 2006

Related U.S. Application Data

(63) Continuation of application No. 09/674,008, filed as application No. PCT/JP99/02207 on Apr. 26, 1999, now Pat. No. 7,047,149.

(30) Foreign Application Priority Data

Apr. 28, 1998    (JP) ................... 10-134649

(51) Int. Cl.
*G01C 17/00*    (2006.01)
(52) U.S. Cl. ....................... 702/150; 702/32
(58) Field of Classification Search ............ 702/150, 702/32
See application file for complete search history.

(56) References Cited

U.S. PATENT DOCUMENTS 4,975,636 A    12/1990    Desautels 5,039,937 A    8/1991    Mandt et al.

(Continued)

FOREIGN PATENT DOCUMENTS

EP    0614645    9/1994

(Continued)

OTHER PUBLICATIONS

Maki et al., "Spatial and temporal analysis of human motor activity using noninvasive NIR topography," Med. Phys. 22 (12), pp. 1997-2000, Dec. 1995.

(Continued)

*Primary Examiner*—John E. Barlow, Jr.
*Assistant Examiner*—Stephen J. Cherry
(74) *Attorney, Agent, or Firm*—Mattingly, Stanger, Malur & Brundidge, P.C.

(57)    ABSTRACT

In order to provide an optical measurement system and an optical measurement method which is suitable for optically measuring a body to be inspected and easily obtaining an image of a desired item based on information obtained by the measurement, an optical measurement method including an initial display process for selectively instructing any one of selection of optical measurement, analysis of said optical measurement result and completion of a program; a process for inputting items of condition including a measurement mode; a process for displaying a light irradiation position and a light detection position and a state expressing measurement position relationship together with said mode; a process for instructing to form a file for storing said optical measurement result; a process for instructing a measurement condition to detect light signals from the inside of a body to be inspected which is irradiated by a multi-wavelength multi-channel; and a process for displaying said signals for each channel detected according to said instructed result.

3 Claims, 22 Drawing Sheets

U.S. PATENT DOCUMENTS

| | | |
|---|---|---|
| 5,161,535 A | 11/1992 | Short et al. |
| 5,517,105 A | 5/1996 | Holzwarth |
| 2001/0018554 A1 | 8/2001 | Yamashita et al. .......... 600/178 |

FOREIGN PATENT DOCUMENTS

| | | |
|---|---|---|
| JP | 60-72542 | 4/1985 |
| JP | 62-231625 | 10/1987 |
| JP | A-63-015050 | 1/1988 |
| JP | A-63-0150050 | 1/1988 |
| JP | 63-277038 | 11/1988 |
| JP | 1-202384 | 8/1989 |
| JP | 5-220142 | 8/1993 |
| JP | A-05-220142 | 8/1993 |
| JP | 06-154227 | 6/1994 |
| JP | 6-154227 | 6/1994 |
| JP | 07-079935 | 3/1995 |
| JP | 7-79935 | 3/1995 |
| JP | A-07-136142 | 5/1995 |
| JP | 09-034542 | 2/1997 |
| JP | 09-098972 | 4/1997 |
| JP | 9-98972 | 4/1997 |
| JP | 9-149903 | 6/1997 |
| JP | 9-262217 | 10/1997 |
| JP | 09-262217 | 10/1997 |
| JP | 10/14900 | 1/1998 |
| JP | 10-014900 | 1/1998 |
| WO | WO 96/20638 | 7/1996 |
| WO | WO 98-10698 | 3/1998 |

OTHER PUBLICATIONS

Patent Abstracts of Japan, vol. 1997, No. 08, Aug. 29, 1997 for JP 09 98872.

Patent Abstracts of Japan, vol. 1997, No. 10, Oct. 31, 1997 for JP 09 149903.

Patent Abstracts of Japan, vol. 1995, No. 06, Jul. 31, 1995 for JP 07 079935.

Patent Abstracts of Japan, vol. 018, No. 101, Feb. 18, 1994 for JP 05-300887.

⊘ IRRADIATION POSITIONS
○ DETECTION POSITIONS
☐ MEASUREMENT POSITIONS

OPTICAL MEASUREMENT INSTRUMENT AND OPTICAL MEASUREMENT METHOD

This application is a continuation of U.S. application Ser. No. 09/674,008, filed Oct. 24, 2000, which is a PCT National Stage Application of PCT/JP99/02207, filed Apr. 26, 1999, now U.S. Pat. No. 7,047,149 which claims priority from Japanese Patent Application 10-134649, filed Apr. 28, 1998, the entirety of which are incorporated herein by reference.

BACKGROUND OF THE INVENTION

The present invention relates to an optical measurement system and an optical measurement method, and particularly, to an optical measurement system which is suitable for optically measuring the inside of a biological body and imaging the inside of the biological body based on information signals obtained by the measurement.

A technology of easily measuring the inside of a biological body without affecting any ill effect on the biological body is desired in the field of clinical treatment. Measurement using light is very effective for this desire. The first reason is that oxygen metabolism inside the biological body corresponds to a concentration of specific pigments (hemoglobin, cytochrome a a3, myoglobin and so on), that is, light absorbents in the biological body, and the concentration of the pigments can be obtained from an amount of absorbed light (in a wavelength band from visible light to near-infrared light). The second reason is that light can be easily handled using an optical fiber.

Systems making use of the advantage of biological measurement using light are disclosed, for example, in Japanese Patent Application Laid-Open No. 63-277038, in Japanese Patent Application Laid-Open No. 5300887 and so on. In the systems, light having wavelengths from visual light to near-infrared light is irradiated onto a biological body, and an inside of a biological body is measured from the reflected light detected at a position 10 to 50 mm distant from the irradiated position. Further, systems for measuring a CT image of oxygen metabolism from light transmitted a biological body having a thickness of 100 to 200 mm, that is, optical CT systems are disclosed, for example, in Japanese Patent Application Laid-Open No. 60-72542 and in Japanese Patent Application Laid-Open No. 62-231625.

In regard to clinical application of biological body optical measurement, in a case of measuring, for example, a head there are measurement of an activation state of cerebral oxygen metabolism and measurement of a local cerebral hemorrhage. In regard to cerebral oxygen metabolism, it is possible to measure higher order brain functions from motion, senses to thinking. In such measurement, the effect of the measurement can be increased larger by displaying the measured result as an image than by not displaying any image. For example, measurement and display as an image is indispensable for detecting a portion where oxygen metabolism is locally changed.

In a multichannel optical measurement system, it is difficult to speedy detect a channel having a problem unless correspondence between actual measured positions and measured signals is shown to an operator operating the system.

In addition, there have been problems to cause serious results in the field of clinical treatment unless the operator inputs a large amount of measuring conditions before initiating the measurement.

SUMMARY OF THE INVENTION

An object of the present invention is to provide an optical measurement system and an optical measurement method which is suitable for optically measuring a body to be inspected and easily obtaining an image of a desired item based on information obtained by the measurement.

In order to attain the above object, in the present invention, measuring positions and a layout of optical fibers specific in the multi-channel optical measurement system are presented to an operator using a display portion. Further, by adding a function of changing the displayed layout corresponding to a measuring signal, it becomes easy to understand the status of the channels. Furthermore, in the present invention, a limited number of windows for inputting measurement conditions are displayed on the display portion, and measurement conditions in the next level hierarchy are displayed after completion of the inputting.

DETAILED DESCRIPTION OF THE PREFERRED EMBODIMENT

Figure 1:
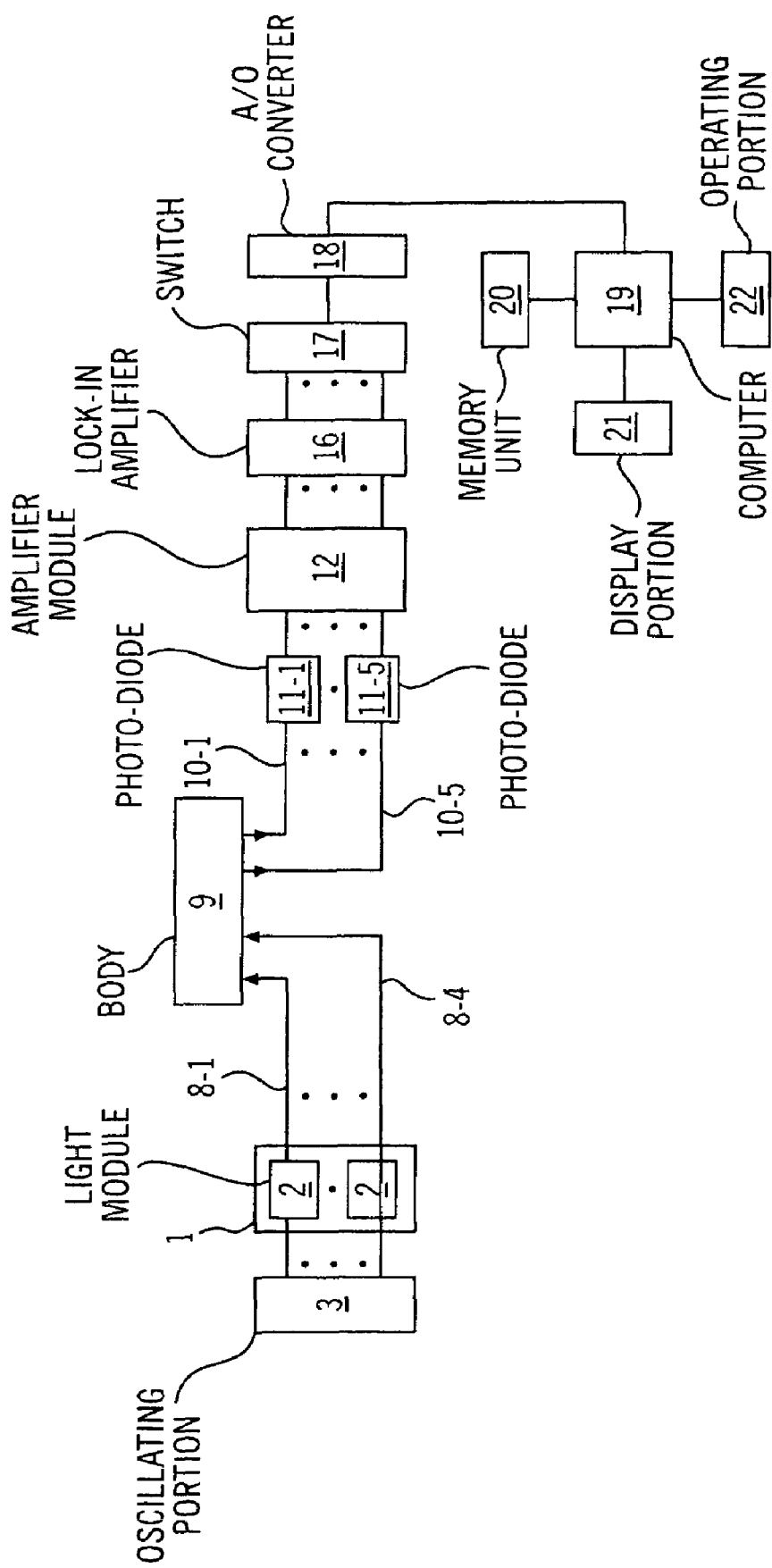
FIG. 1 is a block diagram showing the construction of the main portion of an embodiment of an optical measurement system to which the present invention is applied.

FIG. 1 is a block diagram showing the construction of the main portion of an embodiment of an optical measurement system to which the present invention is applied. The present embodiment is that light is irradiated, for example, on the skin of a head and then light penetrating into and scattered by the body is detected from the skin to image the inside of the cerebrum. In the embodiment, number of measurement channels, that is, number of measurement positions is 12. Of course, the object to be measured is not limited to a head, and the present invention can be applied to the other portions and to an object other than a biological body.

A light source portion 1 is composed of four light modules 2. Each of the light modules is composed of a plurality of semiconductor lasers each emitting light having a different wavelength within a wavelength band from visual to infrared, for example, two semiconductor lasers each emitting light having either of 780 nm or 830 nm wavelength. These values of two wavelengths are not limited to 780 nm and 830 nm, and number of wavelengths is not limited to two. In regard to the light source portion 1, light emitting diodes may be used instead of the semiconductor lasers. The light from all of the eight semiconductor lasers contained in the light source portion 1 is modulated by a oscillating portion 3 composed of eight oscillators having different oscillation frequency, respectively.

Figure 23:
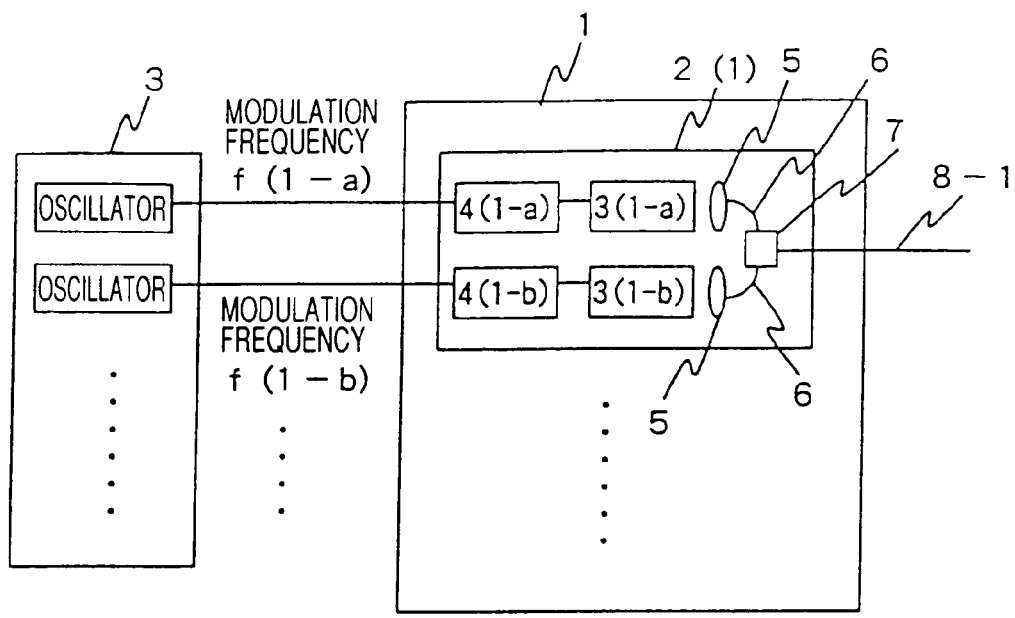
FIG. 23 is a block diagram showing the construction inside the light module of FIG. 1.

FIG. 23 shows the construction inside the light module 2 by taking the light module 2(1) as an example. Semiconductor lasers 3(1-a), 3(1-b) and drive circuits 4(1-a), 4(1-b) for the semiconductor lasers are contained in the light module 2(1). Therein, in regard to the characters in the parentheses, the numeral indicates the number of the light module containing the semiconductor laser or the semiconductor laser drive circuit, and the characters a and b indicate for wavelengths 780 nm and 830 nm, respectively. The semiconductor laser drive circuits 4(1-a), 4(1-b) apply direct current bias current to the semiconductor lasers 3(1-a), 3(1-b), and also apply voltages having frequencies f(1-a), f(1-b) different from each other to the oscillators 3, respectively, to modulate light beams emitted from the semiconductor lasers 3(1-a), 3(1-b). The modulation in the present embodiment is analogue modulation using sinusoidal waves, but of course, digital modulation using rectangular waves having time intervals different from each other may be used. Each of the light beams modulated as described above is introduced into each of optical fibers 6 through each of condenser lenses 5 for each of the semiconductor lasers. Each of the light beams of the two wavelengths introduced into each of the optical fibers is introduced into an optical fiber, for example, an irradiation optical fiber 8-1 by an optical fiber coupler 7. The two-wavelength light beams from the light modules are introduced into the irradiation optical fibers 8-1 to 8-4, respectively, and irradiated onto four different irradiation positions on the surface of a body 9 to be inspected out of the other ends of the irradiation optical fibers. Light reflected from the body to be inspected is detected by detecting optical fibers 10-1 to 10-5 arranged at five detecting positions. An end surface of each of the optical fibers is softly in contact with the surface of the body 9 to be inspected, that is, the optical fiber is attached to the body 9 to be inspected using, for example, a probe described in Japanese Patent Application Laid-Open No. 9-149903.

Figure 24:
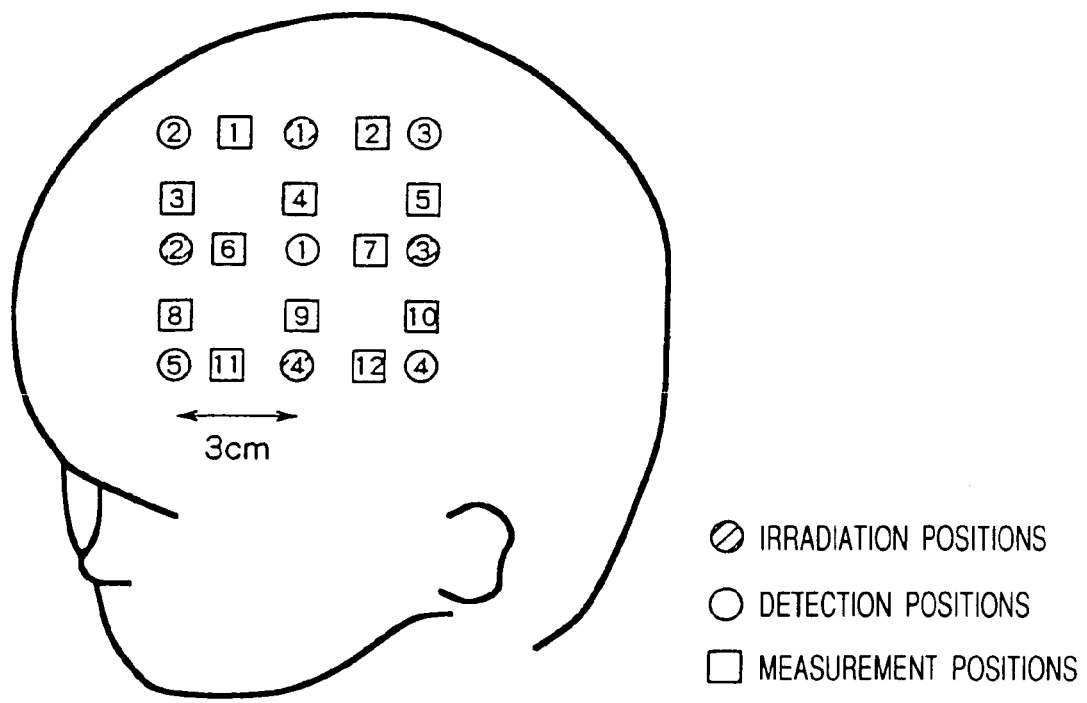
FIG. 24 is a view showing an example of a geographical arrangement of irradiation positions and detecting positions on a surface of a body to be inspected.

FIG. 24 is a view showing an example of a geographical arrangement of the irradiation positions 1 to 4 and the detecting positions 1 to 5 on a surface of the body 9 to be inspected. In the present embodiment, the irradiation position and the detecting position are alternatively arranged on a square lattice. Assuming that the middle position between the irradiation position and the detecting position adjacent to each other is a measured position, number of measured positions, that is, number of measurement channels is 12 because there are 12 combinations of the irradiation position and the detecting position adjacent to each other. The arrangement of the light irradiation positions and the detecting positions is described, for example, in Japanese Patent Application Laid-Open No. 9-149903 and an article entitled "Near-infrared topographic measurement system: Imaging of absorbers localized in a scattering medium" by Yuichi Yamashita et al., Review of Scientific Instrument, Volume 67, pages 730-732. It is reported, for example, in an article entitled "Intracerebral penetration of infrared light" by P. W. Mccormic et al., Journal of Neurosurgery, Volume 76, pages 315-318 that when the interval between the irradiation position and the detecting position adjacent to each other is set to 3 cm, light detected at each of the detecting positions penetrates though the skin and the skull and has information.

From the above, by setting twelve measurement channels under the arrangement of the irradiation and the detecting positions, a cerebrum in an area of 6 cm×6 cm can be measured as a whole. Although the present embodiment shows the case where the number of measurement channels is 12 in order to simplify the explanation, the measurement area can be easily expanded by further increasing numbers of the light irradiation positions and the light detecting positions arranged in a lattice to further increase number of measurement channels.

Referring to FIG. 1, the reflected light detected by each of the detecting optical fibers 10-1 to 10-5 is detected on the detecting position basis, that is, detected independently in the detecting optical fiber corresponding to each of the detecting positions using the five light detectors, for example, using the photo-diodes 11-1 to 11-5. The photo-diode is preferably an avalanche photo-diode which can realize high sensitive light measurement. Further, a photo-multiplier tube may be used as the light detector. After converting the light signal into an electric signal by the photo-diode, a modulated signal corresponding to both of the irradiation position and the wavelength is selectively detected by the lock-in amplifier module 12 composed of a plurality of circuits for selectively detecting a modulated signal, for example, a plurality of lock-in amplifiers. Although in the present embodiment the lock-in amplifiers are shown as the modulated signal detecting circuits coping with the case of analogue modulation, digital filters or digital processors for detecting the modulated signals are used in a case of using digital modulation.

Figure 25:
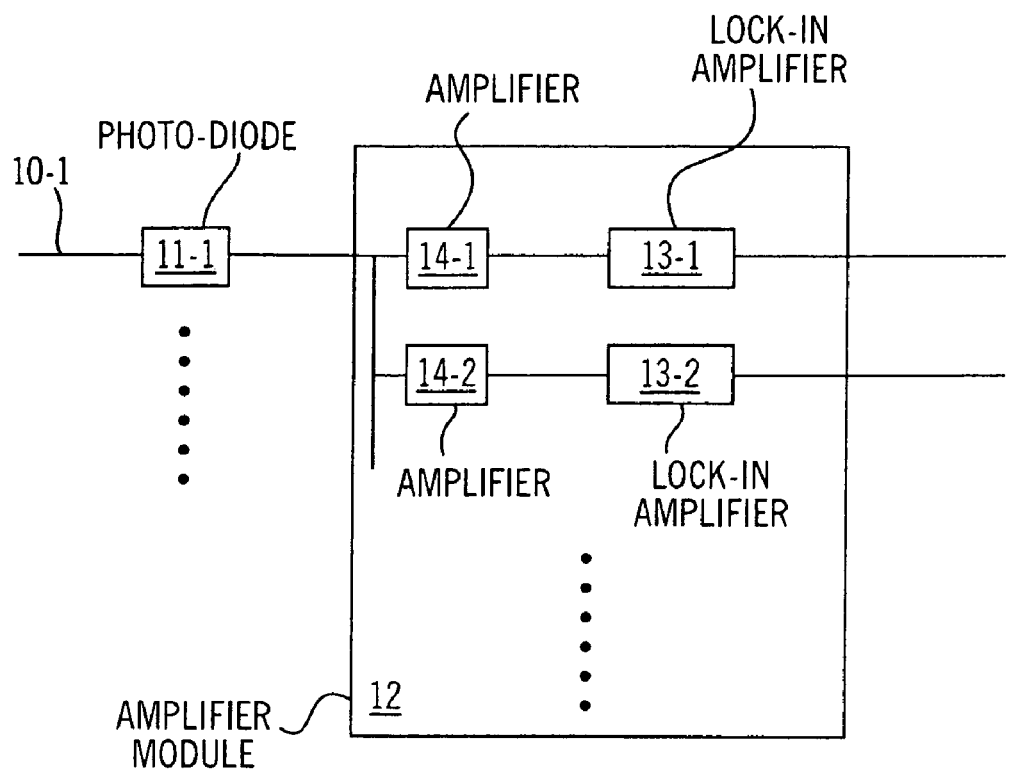
FIG. 25 is a block diagram showing the construction of lock-in amplifier module of FIG. 1.

FIG. 25 is a block diagram showing the construction of lock-in amplifier module of FIG. 1. Initially, explanation will be made on modulated signal separation of the detected signal detected by the photo-diode 11-1 at the position 1 in FIG. 24. At the "detecting position 1", the light irradiated at the "light irradiation position 1", at the "light irradiation position 2", at the "light irradiation position 3" and at the "light irradiation position 4" adjacent to the detecting position 1 can be detected, and accordingly the "measured position 4", the "measured position 6", the "measured position 7" and the "measured position 9" in FIG. 24 are positions to be measured. Here, the detected signal detected by the photo-diode 11-1 at the "position 1" includes eight signal components having the modulation frequencies of f(1-$a$), f(1-$b$), f(2-$a$), f(2-$b$), f(3-$a$), f(3-$b$), f(4-$a$) and f(4-$b$) corresponding to the two-wavelength light each irradiated onto the "irradiation position 1", the "irradiation position 2", the "irradiation position 3" and the "irradiation position 4". The light signals containing the eight signal components are introduced into the eight lock-in amplifiers 13-1 to 13-8 through the 8 amplifiers 14-1 to 14-8. Modulation frequency signals of f(1-$a$), f(1-$b$), f(2-$a$), f(2-$b$), f(3-$a$), f(3-$b$), f(4-$a$) and f(4-$b$) are given to the 8 lock-in amplifiers 13-1 to 13-8 as reference signals, respectively. Therefore, the light signal components of 780 nm and 830 nm wavelengths irradiated onto the "irradiation position 1" are selectively separated by the lock-in amplifiers 13-1 and 13-2; the light signal components of 780 nm and 830 nm wavelengths irradiated onto the "irradiation position 2" are selectively separated by the lock-in amplifiers 13-3 and 13-4; the light signal components of 780 nm and 830 nm wavelengths irradiated onto the "irradiation position 3" are selectively separated by the lock-in amplifiers 13-5 and 13-6; and the light signal components of 780 nm and 830 nm wavelengths irradiated onto the "irradiation position 4" are selectively separated by the lock-in amplifiers 13-7 and 13-8.

In regard to the detecting signals detected by the photo-diodes 11-2 to 11-5 at the "detecting position 2", at the "detecting position 3", at the "detecting position 4" and at the "detecting position 5", respectively, the desired light signal components are similarly selectively separated to be lock-in detected. That is, the light signal detected by the photo-diode 11-2 at the "detecting position 2" is introduced into the four lock-in amplifiers 13-9 to 13-12 through the four amplifiers 14-9 to 14-12, and the light components of 780 nm and 830 nm wavelengths irradiated at the "irradiation position 1" and the light components of 780 nm and 830 nm wavelengths irradiated at the "irradiation position 2" each are selectively separated to be lock-in detected; the light signal detected by the photo-diode 11-3 at the "detecting position 3" is introduced into the four lock-in amplifiers 13-13 to 13-16 through the four amplifiers 14-13 to 14-16, and the light components of 780 nm and 830 nm wavelengths irradiated at the "irradiation position 1" and the light components of 780 nm and 830 nm wavelengths irradiated at the "irradiation position 3" each are selectively separated to be lock-in detected; the light signal detected by the photo-diode 11-4 at the "detecting position 4" is introduced into the four lock-in amplifiers 13-14 to 13-20 through the four amplifiers 14-14 to 14-20, and the light components of 780 nm and 830 nm wavelengths irradiated at the "irradiation position 3" and the light components of 780 nm and 830 nm wavelengths irradiated at the "irradiation position 4" each are selectively separated to be lock-in detected; and the light signal detected by the photo-diode 11-5 at the "detecting position 5" is introduced into the four lock-in amplifiers 13-21 to 13-24 through the four amplifiers 14-21 to 14-24, and the light components of 780 nm and 830 nm wavelengths irradiated at the "irradiation position 2" and the light components of 780 nm and 830 nm wavelengths irradiated at the "irradiation position 4" each are selectively separated to be lock-in detected.

It can be understood from FIG. 24 that in the case where the detecting positions are the "detecting position 2"; the detecting position 3", the "detecting position 4" and the "detecting position 5", the positions to be measured are the "measured position 1" and the "measured position 3", the "measured position 2" and the "measured position 5", the "measured position 10", and the "measured position 8" and the "measured position 11".

As described above, in the case where number of the wavelengths is two and number of the measured positions is twelve, twenty-four of the lock-in amplifiers 13-1 to 13-24 in total are used in the lock-in amplifier module 12. Each of the analogue signals output from the lock-in amplifiers 13-1 to 13-24 (channel 1 to 24) is accumulated for a preset time by a sample hold circuit of the channel corresponding to the sample hold circuit module 16. After completion of the accumulation, the switch (multiplexer) 17 is sequentially switched to convert the signal accumulated in each of the sample hold circuits to a digital signal, for example, by a 12-bit analogue/digital converter (A/D converter) 18, and the converted signals in all of the channels are stored in a memory unit outside a computer 19. Of course, the converted signals may be stored in a memory unit inside the computer 19.

The channel number corresponds to the address of the memory unit 15 with a one to one relation.

In a case of not using the sample hold circuit module 16, the switch 17 is repetitively switched at high speed. The analogue signal of each channel is converted into a digital signal using the analogue/digital converter 18 every switching to be accumulated in the memory unit 20, and the digital signals acquired a preset number of times are averaged on the channel basis to be stored in the memory unit 20. This method can reduce noise of high frequency components.

Based on the data stored in the computer 19, change in the concentration of oxygenated hemoglobin and change in the concentration of deoxygenated hemoglobin associated with cerebral activity, and further change in the concentration of total hemoglobin as the total concentration of hemoglobin are calculated through the method described in, for example, Japanese Patent Application Laid-Open No. 9-19408 and in an article entitled "Spatial and temporal analysis of human motor activity using noninverse NIR topography" by Atsushi Maki et al., Medical Physics, Volume 22, pages 1997-2005 (1995), and the result such as a topography image or the like is displayed on the display portion 20.

Figure 26:
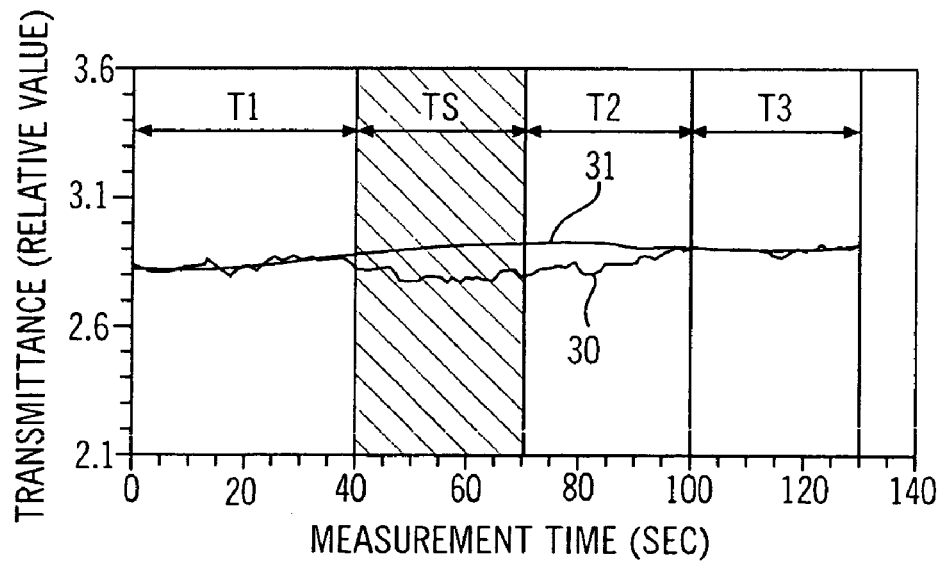
FIG. 26 is a graph showing an example of time variation of a measured signal at a detecting position and time variation of a predicted no-load signal obtained from the measured signal.

Referring to FIG. 1, the computer 19 may be a personal computer. An operating portion 22 is connected to the computer 19, and the operating portion includes a keyboard, a mouse and so on for inputting and outputting various kinds of information and for adding and deleting data. FIG. 26 is a graph showing time variation of a measured signal 30 at a detecting position and of a predicted no-load signal 31 obtained from the measured signal. The graph is displayed on the display portion 21, and the abscissa indicates measurement time and the ordinate indicates an amount of relative change in hemoglobin concentration, that is, the amount corresponding to change in hemoglobin concentration at a specific position in a cerebrum caused by motion of a specific position of a body (for example, motion of a part of the body such as a finger or the like). The predicted no-load signal 31 is obtained from the measured signal 30 by fitting an arbitrary function to the measured signal 31 in the time before loading T1 and the time after applying load T3 except the signals in the time applying load (loading time) Tt and the time until the signal returns the original value (relaxation time) T2 through the least-squares method. In the present embodiment, the processing is performed by using a secondary-order linear polynomial for the arbitrary function and by setting T1=40 seconds, T2=30 seconds and T3=30 seconds.

Figure 27:
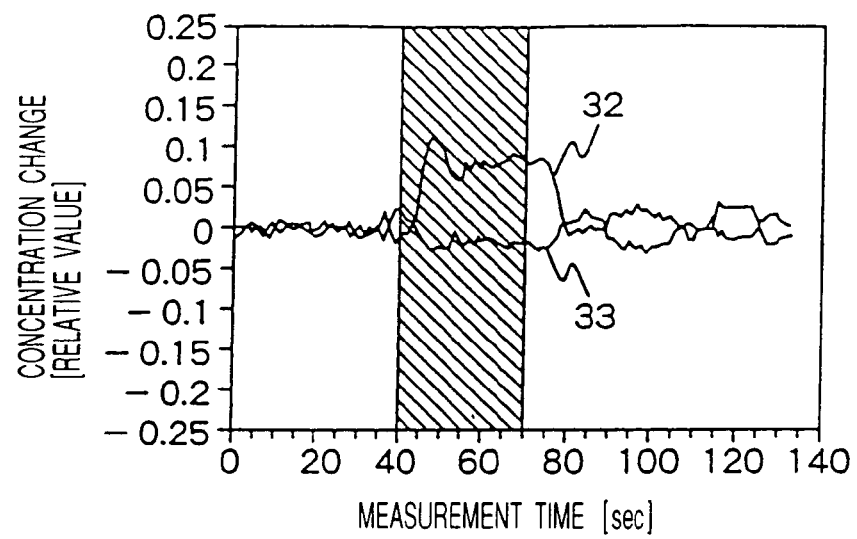
FIG. 27 is a graph showing an example of time variation of an amount of relative change in concentrations of oxygenated hemoglobin and deoxygenated hemoglobin at a measurement position.

FIG. 27 shows an example of time variations of an amount of relative change in concentrations of oxygenated hemoglobin and an amount of relative change in concentrations of deoxygenated hemoglobin at a measurement position. The graph is displayed on the display portion 21. The abscissa indicates measurement time and the ordinate indicates relative amounts of change in the concentrations. The time illustrated by the hatched area is a load applying time (a period of moving a finger of right hand). In regard to the relative amount of change shown in FIG. 26, the relative amounts of changes in oxygenated hemoglobin and in deoxygenated hemoglobin ($H_bO_2$, $H_b$) associated with load application is calculated based on the non-load signal 31 and the predicted non-load signal 32 through a predetermined calculation processing.

Figure 28:
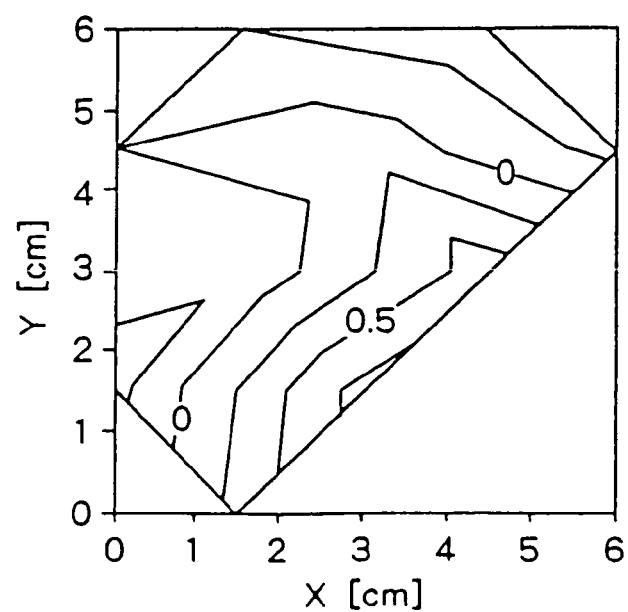
FIG. 28 is a view showing a contour image (a topography image) produced from time variation of an amount of relative change in a concentration of oxygenated hemoglobin at each measurement position when motion of left-hand fingers of a person to be inspected is used as a load.
Figure 29:
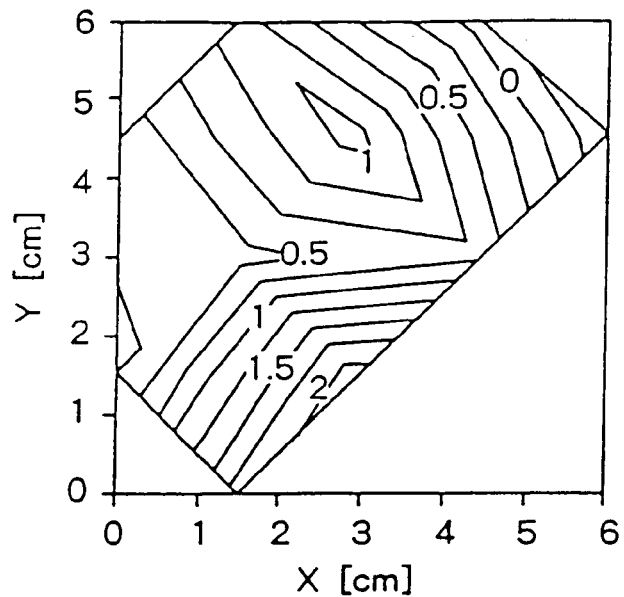
FIG. 29 is a view showing a contour image (a topography image) produced from time variation of an amount of relative change in a concentration of oxygenated hemoglobin at each measurement position when motion of right-hand fingers of a person to be inspected is used as a load.

Each of FIG. 28 and FIG. 29 shows a contour image (a topography image) produced from the time variation of the relative amount of change in a concentration of oxygenated hemoglobin at each measurement position displayed in the display portion 21 when motion of left-hand or right-hand fingers of a person to be inspected is used as load, respectively. The topography image is formed by calculating an integrated value with time (an averaged value with time may be acceptable) of the signal of relative amount of change 32 in the load applying time (the hatched period in FIG. 27) by the processing portion 19, and linearly interpolating between the measured positions in the X-axis direction and the Y-axis direction. As the topography image, a monochrome grayscale image or a color identifying image may be acceptable instead of the contour image shown in FIG. 28 and FIG. 29. It can be understood from FIG. 28 and FIG. 29 that the oxygenated hemoglobin concentration is clearly increased at a specific position when right-hand finger is moved.

By displaying such information of spatial distribution as an image, recognition of the measured result can be made speedy and easy. Further, although the images shown in FIG. 28 and FIG. 29 are formed using the time-integrated values of the relative amount of change in concentration during the load apply time period, a similar topography image can be formed using relative amounts of change in oxygenated hemoglobin concentration at the measured positions every measuring time performed at a time. By displaying the plurality of formed topography images in order of measured time or as a moving picture, the time variation of the relative amount of change in the oxygenated hemoglobin concentration can be understood.

Further, by calculating a self-correlation function of the time variation of the relative amount of change in oxygenated hemoglobin concentration at an arbitrary one measured position and a mutual-correlation function of the time variation of the relative amount of change in oxygenated hemoglobin concentration at one and the other measured positions, a topography image for each position can be also formed from the correlation functions. Since the correlation function at each position is a function defined by shifting time by $\tau$, a state of propagation of change in a dynamic blood state can be visualized by forming photography images from the values of the correlation functions shifting by the same time of $\tau$ and displaying the photography images in order of $\tau$ or as a moving picture. Although the description here is made on the relative amount of change in oxygenated hemoglobin concentration as the typical example, the relative amount of change in deoxygenated hemoglobin concentration and the relative amount of change in the total hemoglobin concentration calculated as the sum of the relative amounts of change in oxygenated and deoxygenated hemoglobin concentrations can be similarly formed in the topography images.

Figure 30:
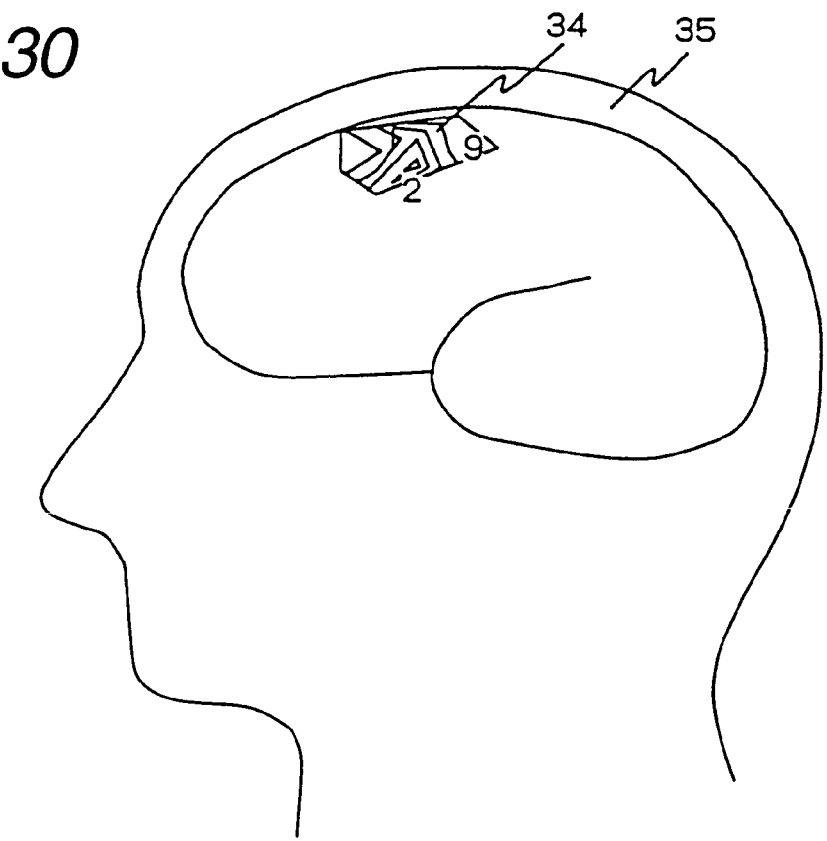
FIG. 30 is a view showing an example of a display superposing a topography image on a cerebrum surface image of a person to be inspected.

FIG. 30 shows an example of a display superposing a topography image 34 formed through the method described above on a cerebrum surface image 35 of a person to be inspected. Since the topography image 34 is change in a dynamic blood state of a cerebrum changing in association with change in a biological function, it is preferable that the topography image is displayed by superposing on the cerebrum surface image. The cerebrum surface image 35 is displayed by being measured by a three-dimensional MRI or a three-dimensional X-ray CT. The topography image 34 is a topography image which is formed by converting the coordinate system so that the coordinates of the measured positions are placed on the surface of the cerebrum, and then interpolating the values between the measured positions. When the formed topography image 34 is displayed by superposing on the cerebral surface image 35, the color of the superposed topography image 34 is made translucent so that the cerebral surface image under the topography image 34 can be seen.

Figure 2:
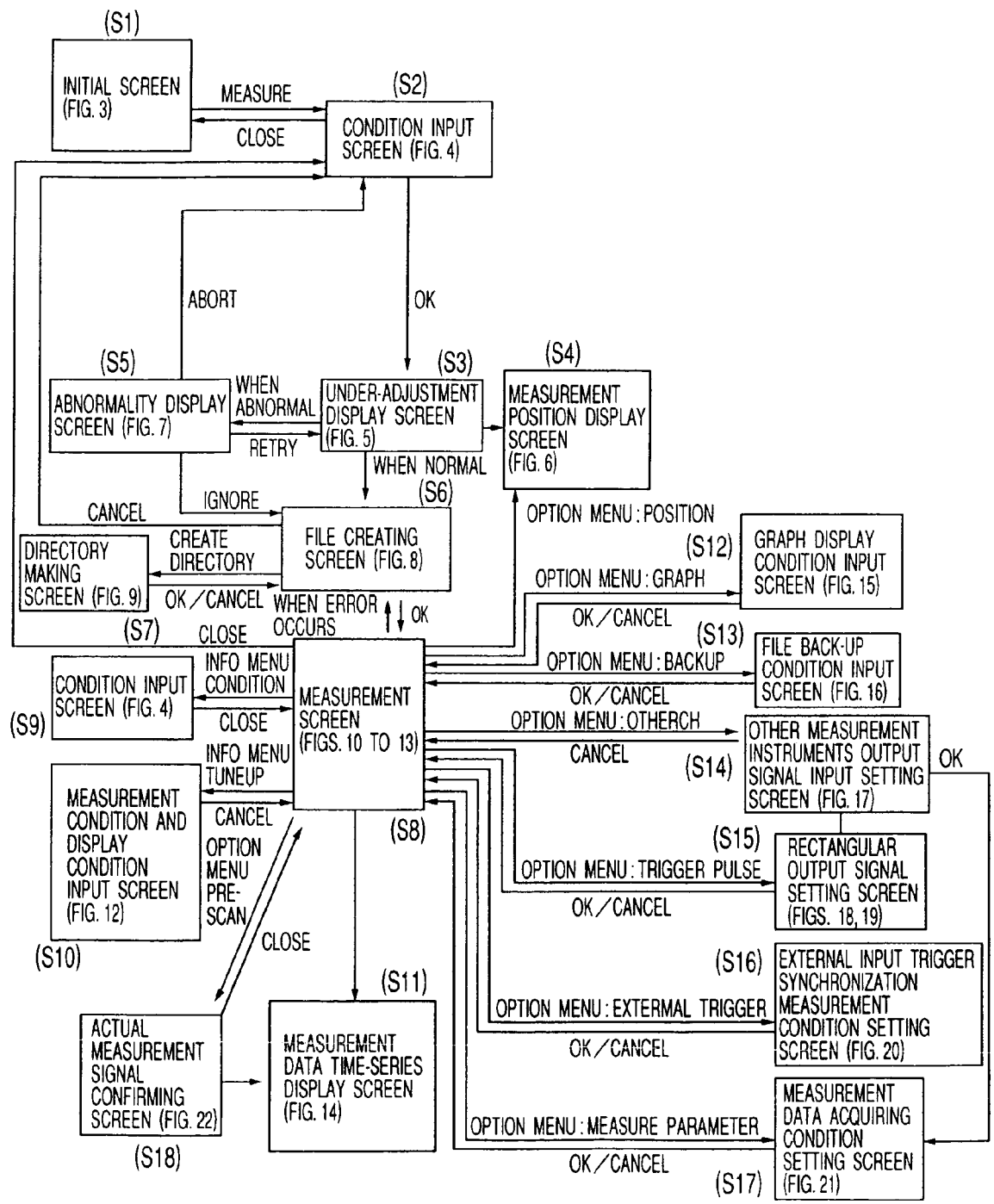
FIG. 2 is a flowchart showing an example of processing flow in accordance with the present invention for measuring a body to be inspected using the optical measurement system shown in FIG. 1.

FIG. 2 is a flowchart showing an example of processing flow in accordance with the present invention for measuring a body to be inspected using the optical measurement system shown in FIG. 1. Operation of the optical measurement system is sequentially performed while an operator is looking at the windows, shown in FIG. 3 to FIG. 22, displayed on a window display screen of the display portion 21.

Figure 3:
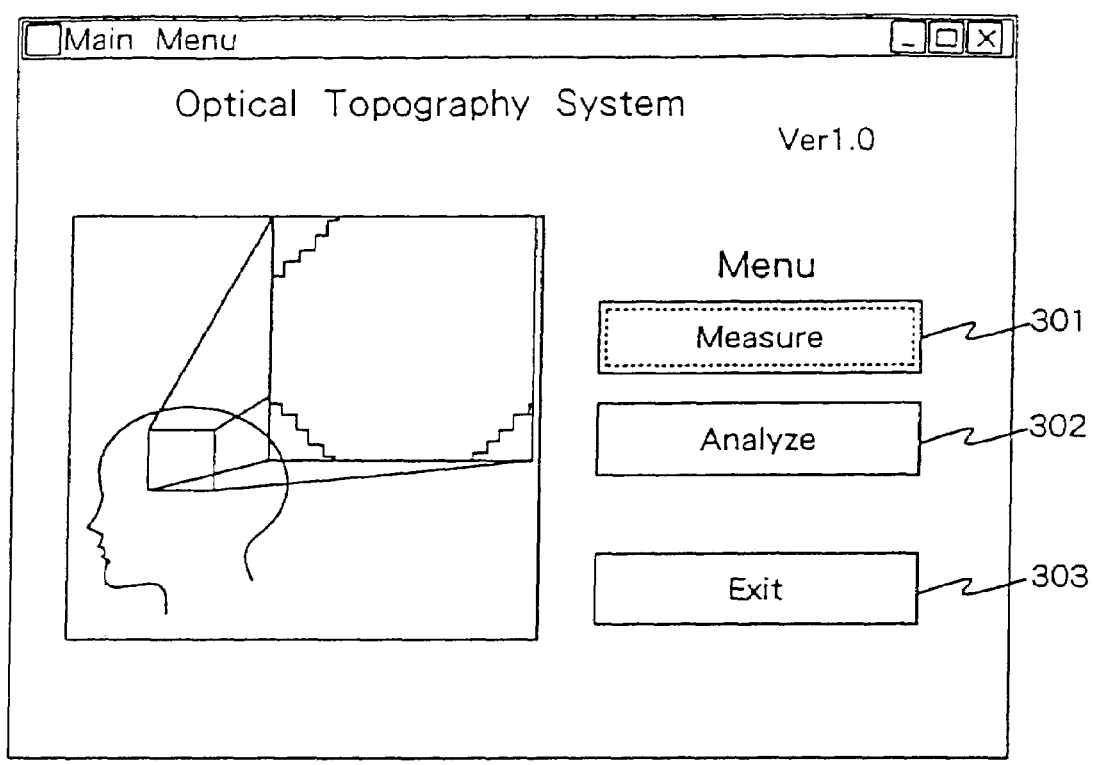
FIG. 3 is a view showing an initial window which is shown on a display portion.

As the operating system of the system is booted, an initial window for selecting main menu shown in FIG. 3 is displayed (S1). Referring to FIG. 3, the processing proceeds to measurement processing when the button 301 is selected, the processing proceeds to data analysis when the button 302 is selected and the program is ended when the button 303 is selected.

Figure 4:
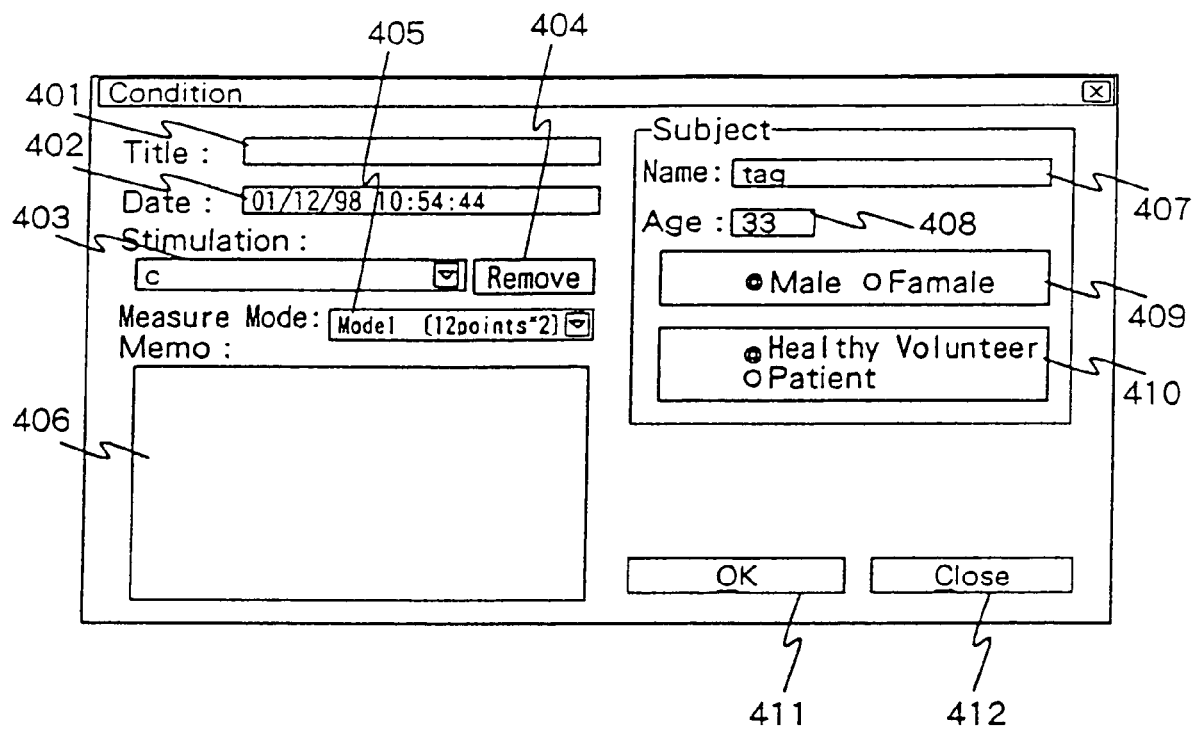
FIG. 4 is a view showing a window for inputting conditions which is shown on the display portion.

Assuming now that the button 301 is selected, the initial window shown in FIG. 3 disappears, and the processing proceeds to the measurement processing to display a window for inputting conditions shown in FIG. 4 is displayed in the middle of the display screen of the display portion 21 (S2). In regard to FIG. 4, meaning and function of each part are as follows.

401: A bar for inputting a title. In detail, a name of inspection to be performed is input.

402: A part for displaying data and time, data and time as displaying the window is displayed by default (automatically displayed numerals or characters).

403: A part for inputting a kind of stimulation (for example, finger motion, writing, speaking, giving medication and so on). A list display button (an inverted delta symbol button) is pushed and then desired items are selected from pre-registered kinds in the list box. The selected kinds are displayed by changing the back color or with reversed characters. The data can be added, deleted and replaced.

404: A kind of item selected in the stimulation input part can be deleted by this button.

405: A part for selecting a measurement mode. The measurement mode is determined by number of measuring channels and number of surfaces to be measured. For example, in a case where number of measurement channels is 1 and number of surfaces to be measured is 2, it is assumed that measurement mode 1 is selected.

406: A part for freely writing memorandum.

407: A part for inputting name of a person to be inspected.

408: A part for inputting age of a person to be inspected.

409: A part for inputting sex of a person to be inspected.

410: A part for inputting a kind of a person to be inspected, that is, a patient or a healthy person.

411: A setting ending button.

412: A button for returning to the initial window.

Figure 5:
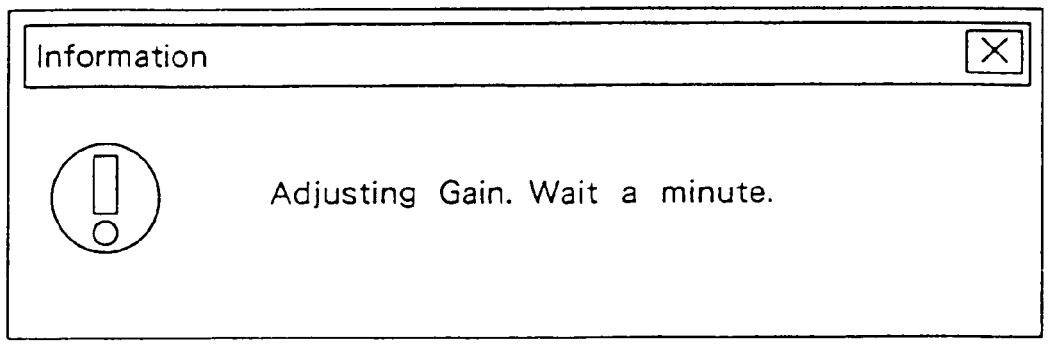
FIG. 5 is a view showing a window for displaying gain adjusting underway which is shown on the display portion.

After inputting and setting the above conditions, by pushing the button 412, the window for inputting conditions disappears and a window for displaying gain adjusting underway shown in FIG. 5 is displayed in the middle of the screen (S3). This expresses that the measurement system is under automatic gain adjusting, and after completion of the adjustment the window for displaying gain adjusting underway disappears and a window for displaying measured positions is displayed in the middle of the display screen (S4). Essentially after now, this window is always displayed at a position in the screen of the display portion 21. By always displaying the window for displaying measured positions, it is possible to easily and speedily understand the correspondence between the many measured signals and the actual measured positions. There, the irradiation optical fibers 8-1 to 8-4 and the detecting optical fibers 10-1 to 10-5 shown in FIG. 1 are generally fixed in a helmet to be put on by the person to be inspected. Therefore, if measuring channel numbers are indicated on the helmet to make the positional relationship between the number shown by the reference character 602 in FIG. 6, recognition of the operator is further assisted.

Figure 6:
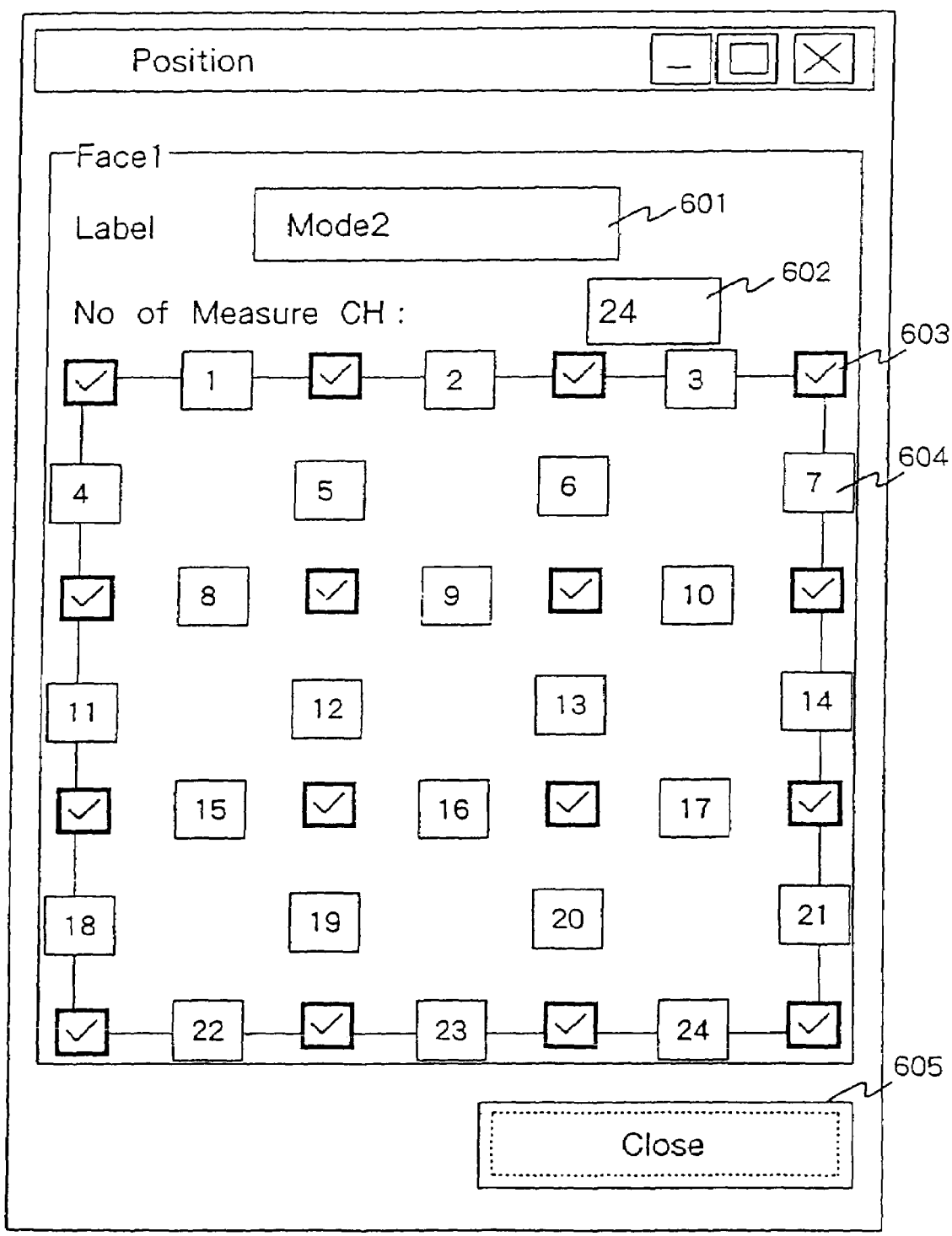
FIG. 6 is a view showing a window for displaying measured positions which is shown on the display portion.

Referring to FIG. 6, the reference character 601 is a part for displaying the selected measuring mode, the displayed window for displaying measured positions corresponds to the measuring mode. The reference character 602 is a part for displaying number of measuring channels of the measured plane. The reference character 603 indicates the setting positions of the irradiation and the detecting optical fibers, that is, the irradiation positions and the detecting positions. The reference character 604 indicates the measuring channel numbers, and the measuring channel number is displayed in green color when the automatic gain adjustment of the measuring channel is well performed.

Figure 7:
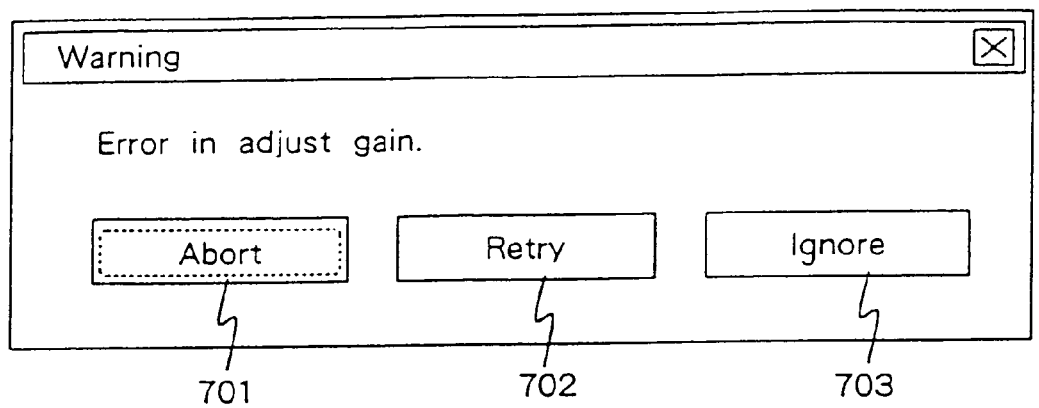
FIG. 7 is a view showing a window for display abnormality which is shown on the display portion.

When there exists at least one measuring channel which is failed in the gain adjustment, the measuring channel number of the measuring channel is displayed in red color. Further, in this case, a window for display abnormality shown in FIG. 7 is displayed near the window for displaying measured positions shown in FIG. 6 (S5). The case where the gain adjustment is failed means that there is possibly a problem in a measured position in the right-hand side or the left-hand side or the upper side or the down side of the channel displayed in red color. Since it is considered that there is a problem in setting of the optical fiber when the red-colored display appears, the optical fiber is required to be reset. Therefore, after resetting the optical fiber, the reference character 701 in FIG. 7 is used when the measurement is aborted by returning to the window of FIG. 3 or FIG. 4. When the button 702 of FIG. 7 is pushed, the window for display abnormality is deleted and the window for displaying gain adjusting underway is displayed to perform the automatic gain adjustment again. When there remains still any abnormality after adjusting gain, the window for displaying gain adjusting underway shown in FIG. 5 is deleted, and the abnormal measuring channel in the window for displaying measured positions shown in FIG. 6 is displayed in red color, and the window for displaying abnormality shown in FIG. 7 is displayed near the window for displaying measured positions shown in FIG. 6. When no abnormality occurs, the window for displaying gain adjusting underway shown in FIG. 5 is deleted, and all the measuring channels in the window for displaying measured positions shown in FIG. 6 are changed to green color, and a window for forming a file shown in FIG. 8 is displayed.

In FIG. 7, the reference character 703 is a button which is pushed when the abnormality is neglected. When the button is pushed, the window for forming a file is displayed (S6) by neglecting the abnormal measuring channel in the window for displaying measured positions shown in FIG. 6 (remaining the red colored display as it is). The window for forming a file shown in FIG. 8 is displayed in the middle of the display screen regardless of presence and absence of abnormality, and the position of the window for displaying measured positions shown in FIG. 6 is moved to a lower left position in the display screen as the window for forming a file shown in FIG. 8 is displayed. By this display method, the operator can always watch the condition to be input.

Figure 8:
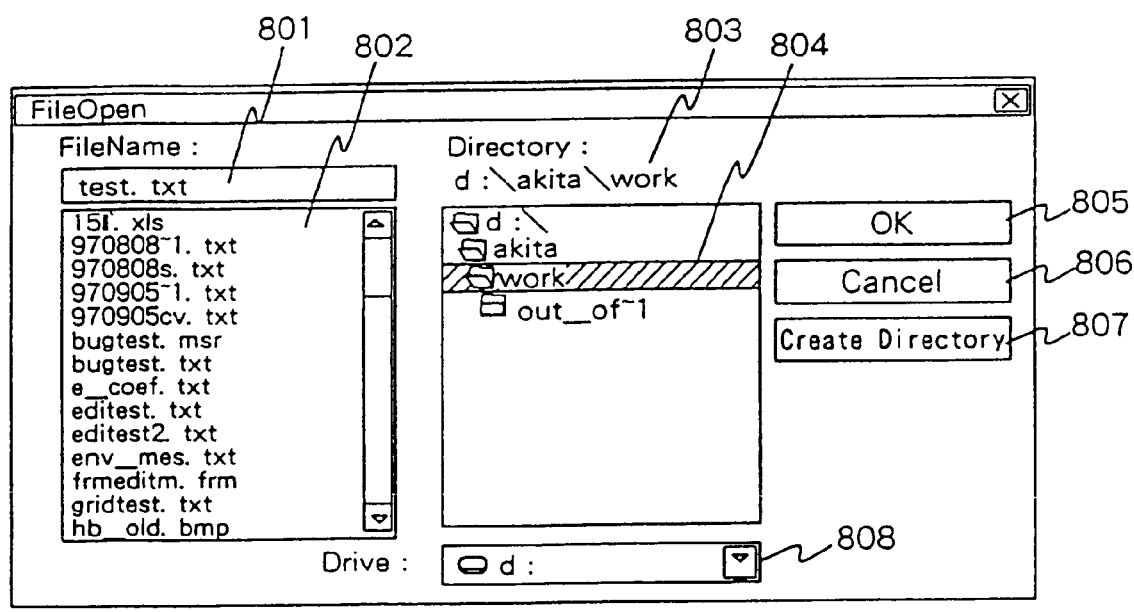
FIG. 8 is a view showing a window for forming a file which is shown on the display portion.

In FIG. 8, meaning and function of each part are as follows.

801: A part for inputting a file name.

802: A part for displaying a list of all files existing in a hierarchy which is selected by the button 804. For example, data names of measurement previously performed are displayed in this part.

803: A part for displaying the present path.

804: A part for displaying a directory list (hierarchy list).

805: A button for giving permission to proceed to measurement process.

806: A pushed button for canceling and returning to the window for inputting conditions of FIG. 4. When the button is pushed, the window for forming a file shown in FIG. 8 and the window for displaying measured positions shown in FIG. 6 are deleted, and the window for inputting conditions shown in FIG. 4 is displayed.

807: A button for displaying the window for creating directory, and the button is used when creating a new directory. When the button is pushed, the window for creating directory is displayed superposing on the window for forming a file shown in FIG. 8 in a slightly shifting state. At that time, the window for creating directory shown in FIG. 9 can not be operated.

808: A button for performing specifying a drive.

Figure 9:
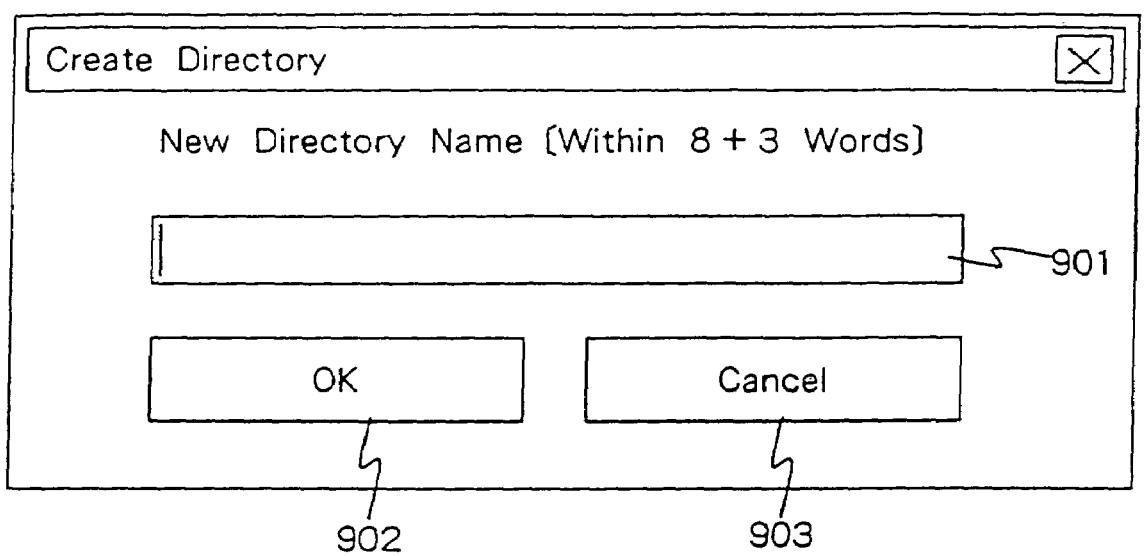
FIG. 9 is a view showing a window for forming a directory which is shown on the display portion.

When the button 807 is pushed, the window for creating directory shown in FIG. 9 is displayed (S7). Referring to FIG. 9, the reference character 901 is a part for inputting name of a directory to be created, the reference character 902 is a button for completing directory creation, and the reference character 903 is a cancel button. When any one of the buttons is pushed, the window for creating directory shown in FIG. 9 is deleted and the processing is returned to the window for forming a file shown in FIG. 8.

Figure 10:
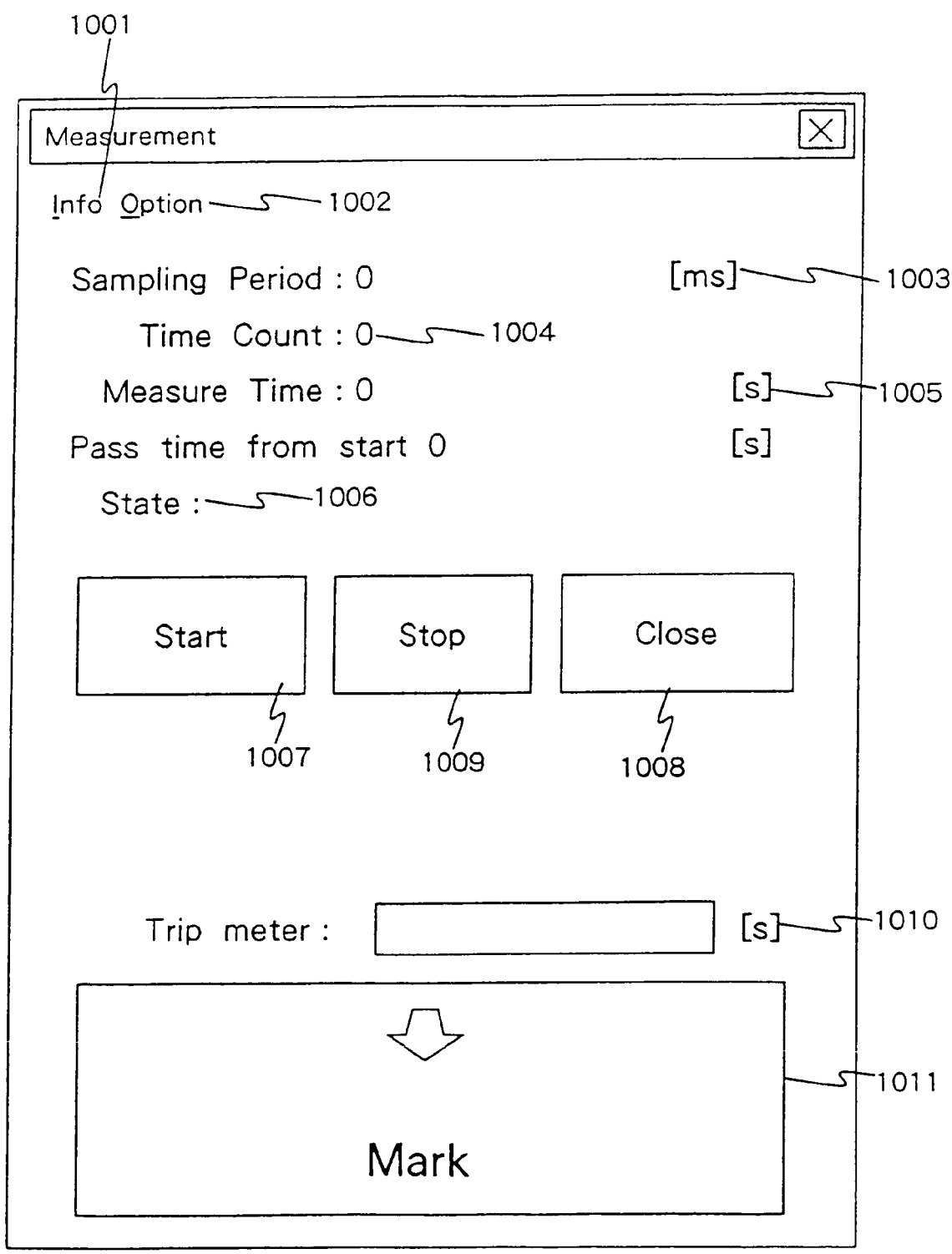
FIG. 10 is a view showing a measurement window which is shown on the display portion.
Figure 14:
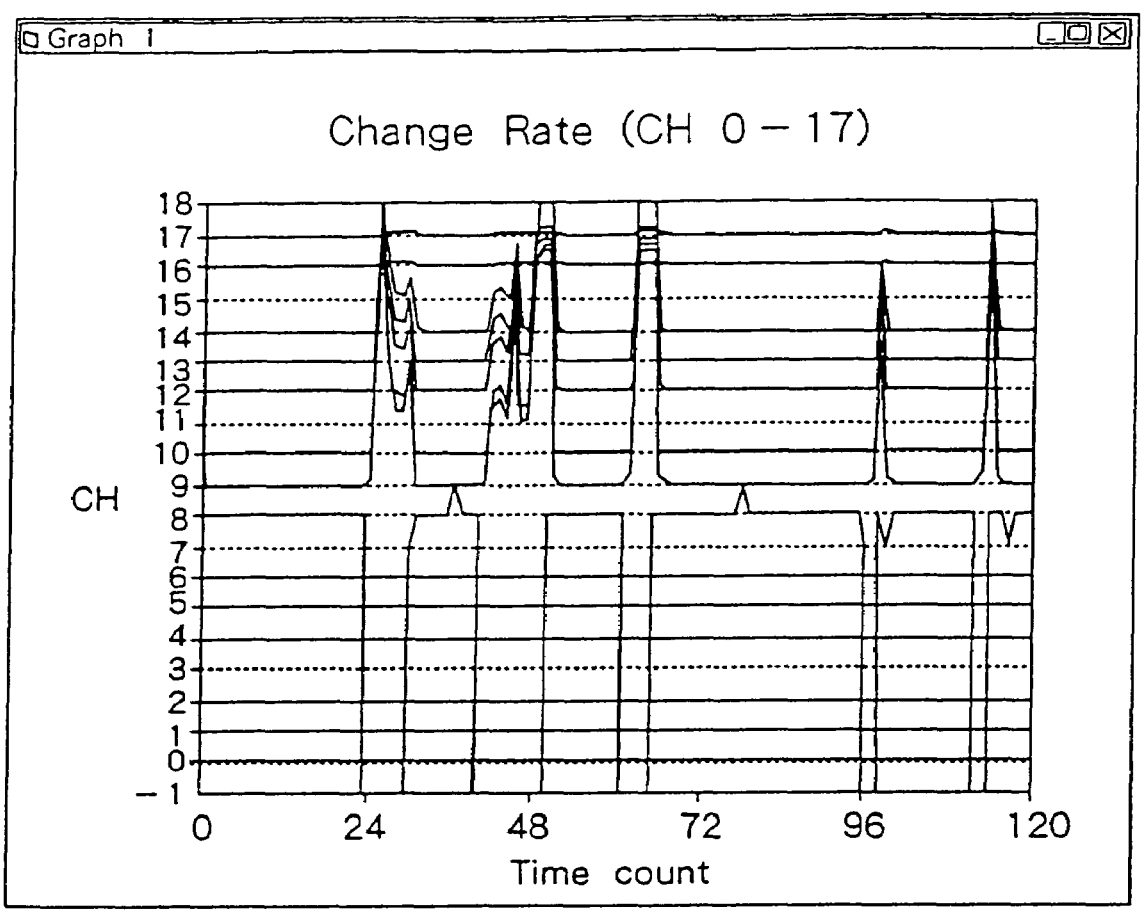
FIG. 14 is a view showing a window for displaying a measurement data time sequence which is shown on the display portion.

Referring to FIG. 8, when the button 805 is pushed, the window for forming a file shown in FIG. 8 is deleted, and a measurement window shown in FIG. 10 is displayed an upper left portion of the display screen (S8), and a window or windows for displaying measurement data time sequence shown in FIG. 14 is or are displayed in a large portion in the right side of the display screen (S11). FIG. 8 is used for controlling execution of measurement. In regard to FIG. 10, meaning and function of each part are as follows.

Figure 11:
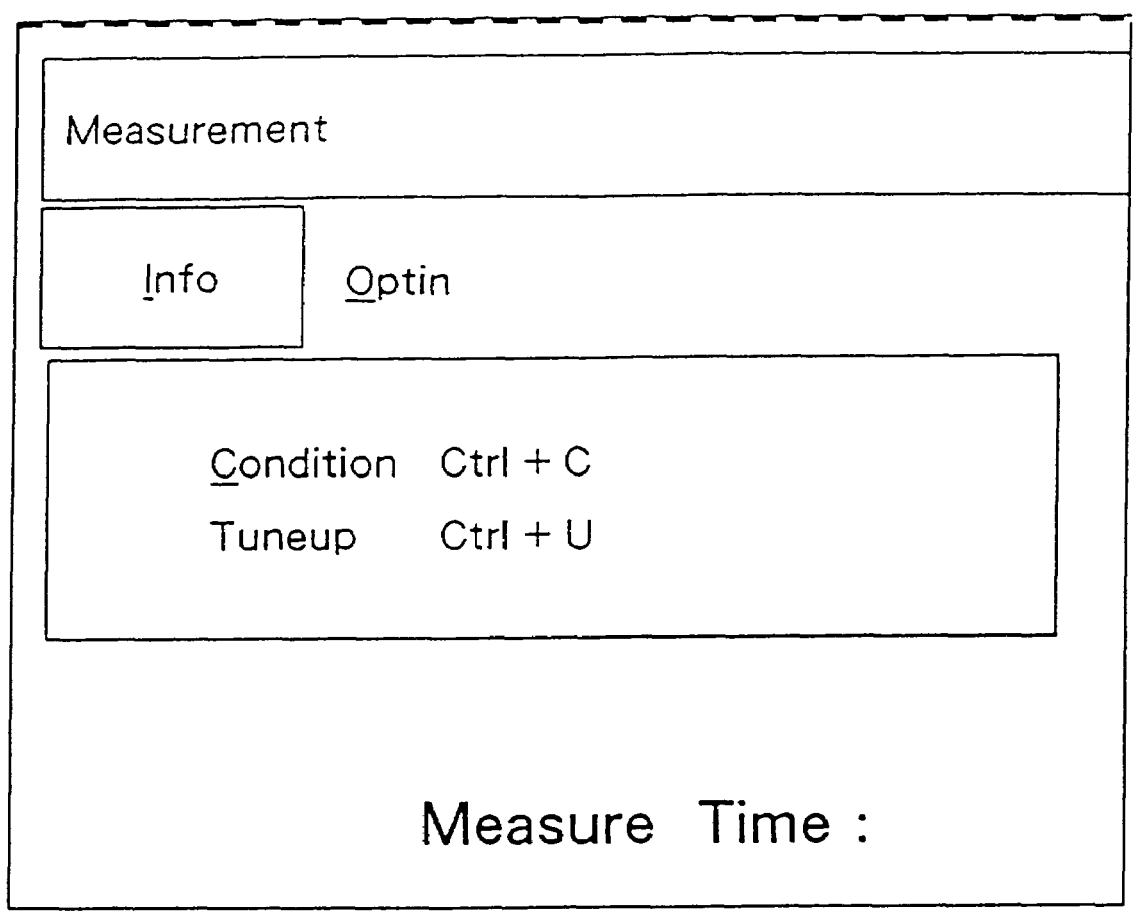
FIG. 11 is a view showing a sub-menu window of Info of FIG. 10 which is shown on the display portion.
Figure 12:
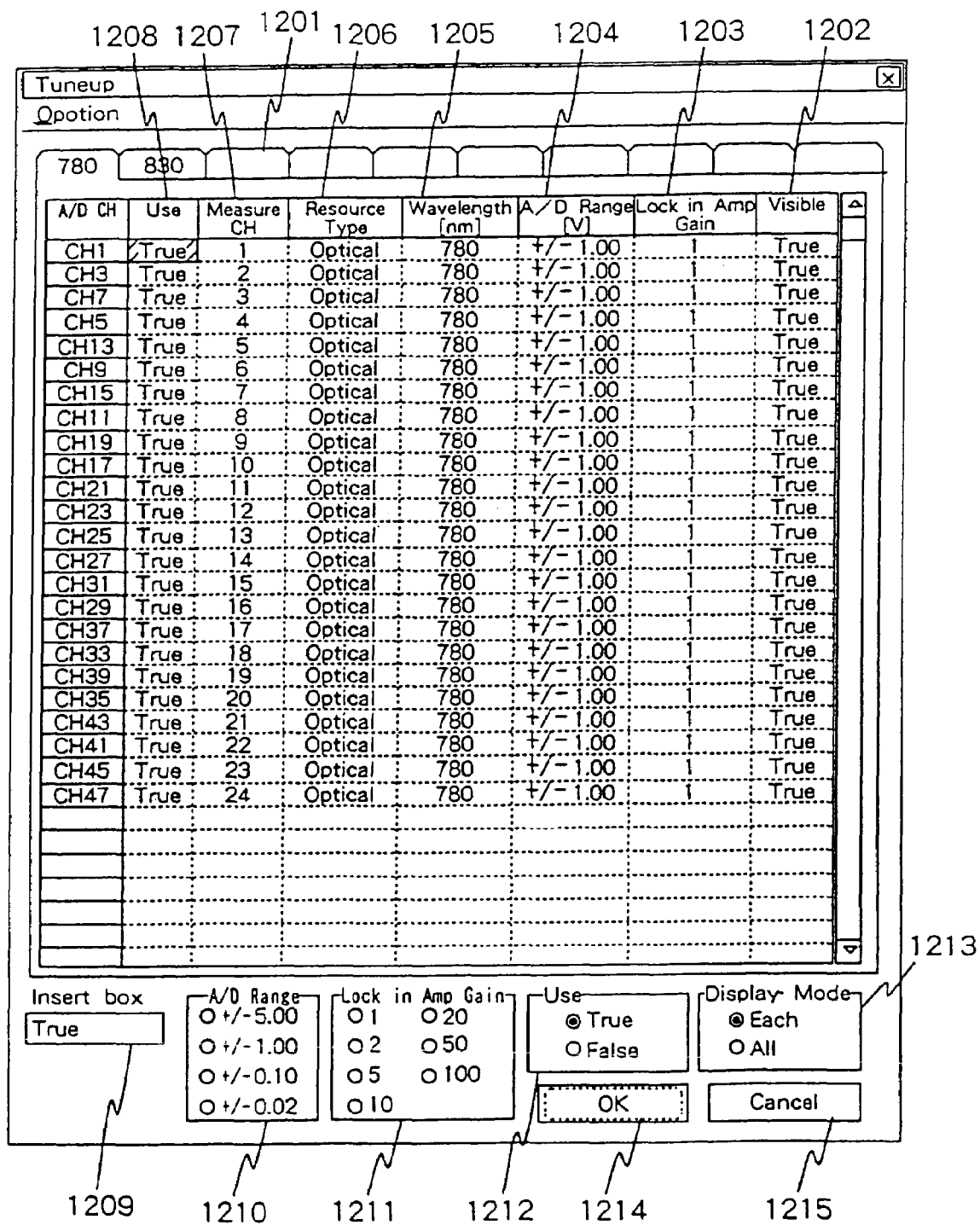
FIG. 12 is a view showing a window for inputting measurement conditions and display conditions which is shown on the display portion.

1001: A button for selecting Info. When Info is selected, a window for selecting Condition or Tuneup as a sub-menu, as shown in FIG. 11. When Condition in sub-menu of FIG. 11 is selected, the window for inputting condition similar to FIG. 4 is displayed (S9). This is for checking the present status or inputting an additional condition. When Tuneup in the sub-menu of FIG. 11 is selected, a window for inputting measuring condition and display condition shown in FIG. 12 is displayed (S12). When the cancel button is pushed in the step 9 or step 10, the window for inputting condition similar to FIG. 4 or the window for inputting measuring condition and display condition shown in FIG. 12 is deleted, and the processing is returned to the measurement window of FIG. 10.

Figure 13:
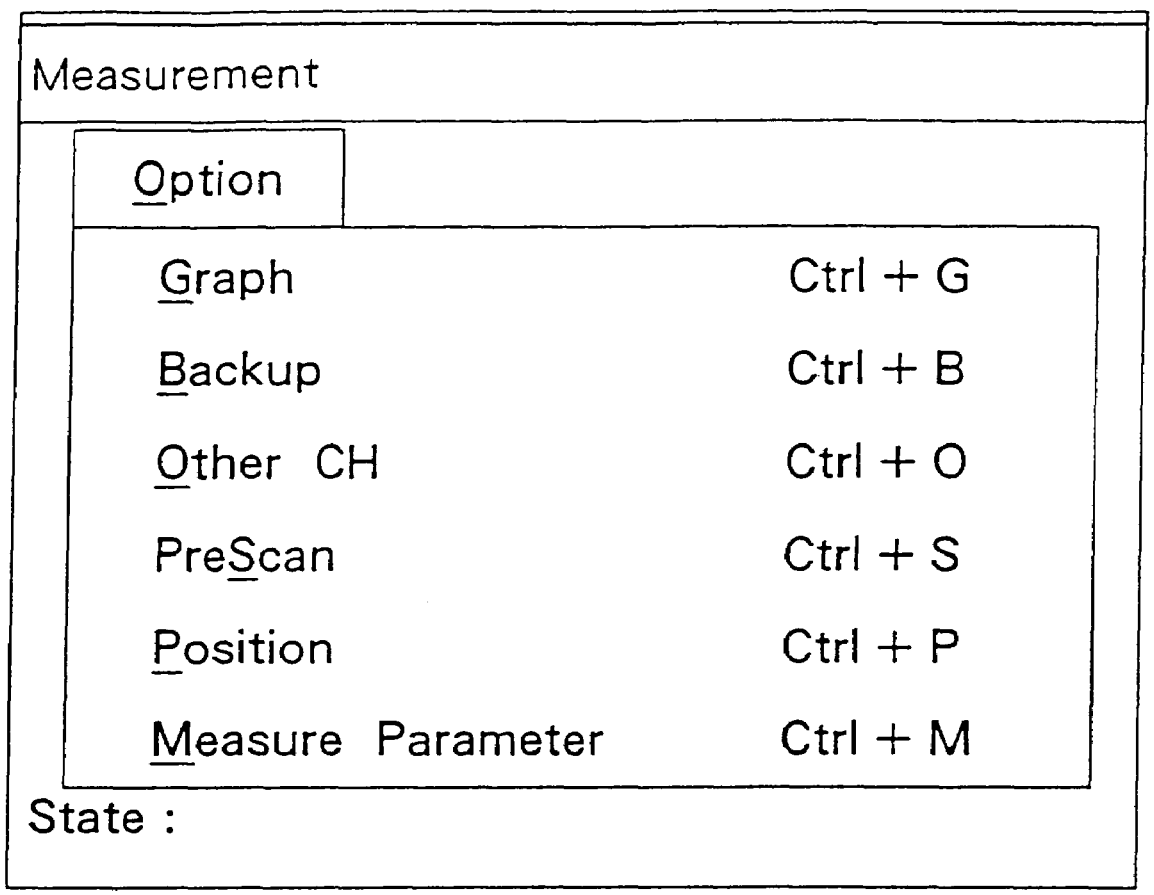
FIG. 13 is a view showing a window of Option of FIG. 10 which is shown on the display portion.

1002: When Option is selected by the button for selecting Option, A sub-menu window shown in FIG. 13 is displayed. Here, graph display conditions for measurement underway, and conditions of a data backup interval and signals output from the other measurement instruments to be described later are input, but there is no need to input every time because there is a learning function to automatically reflecting values which are set at the preceding measurement.

1003: A part for specifying and displaying a data acquisition time interval.

1004: A part for displaying number of data acquisition times (number of sampling times).

1005: A part for displaying a measuring elapsing time.

1006: A part for displaying the next measurement state.

Run: measuring underway

Completion: normal completion of measurement

Overrun: abnormal completion of measurement due to overflow of A/D converter

Stop: abnormal completion of measurement due to the other cause

File error: error in measurement file writing

Backup file error: error in backup file writing

1007: A button for starting measurement. When the button is pushed, measurement is started and measurement data time sequence signal graph is displayed in each axis in FIG. 14 (S11). The displayed graph expresses a change ratio.

1008: A button for completing data acquisition.

1009: A button for completing measurement and inspection.

1010: A part for displaying an elapsing time after pushing Mark button 1011: By this part, there is an advantage in that a stimulating time period can be managed without using any stopwatch.

1011: The Mark button which is for inserting a mark of a vertical line in the graph of FIG. 14 during measurement. This mark is usually input at starting and at completing stimulation as a reference for data analysis, but the mark may be arbitrarily input when an event requiring to record time occurs during measurement. When a mark input signal is supplied from an external device, a mark is displayed in the drawing of FIG. 14 without pushing the button. Moreover, a sound may be generated when the mark input signal is supplied.

In the window for inputting measuring condition and display condition shown in FIG. 12, a measurement condition corresponding to a selected measurement mode is displayed. The measurement condition expresses correspondence to a measuring channel (measuring position), a channel of A/D converter, a wavelength, a signal amplification and so on. Further, specifying of a channel to measure and specifying of a channel to display may be possible. Furthermore, it is possible to instruct to input another signal into a vacant channel. In regard to FIG. 12, meaning and function of each part are as follows.

1201: There are tables showing the measurement conditions and the display conditions for each wavelength using in the selected mode, and a table in regard to a wavelength to be displayed is selected using this tab.

1202: A part for specifying requirement of displaying a graph to display the graph. The word True in the column means displaying the graph, and the word False means not displaying the graph. By pre-selecting graphs not required to be display for individual channels (by clicking a box in the Visible column, the selection is performed to change the back color or to be inversely displayed), and then by specifying a False button of 1212, the selected measurement channel is turned from True to False.

1203: A part for displaying a gain of the lock-in amplifier.

1204: A part for displaying a dynamic range of the A/D converter. In the columns of the parts 1203 and 1204, the values determined by the automatic gain adjustment are displayed.

1205: A part for displaying wavelength.

1206: A part for displaying a kind of signal. The word Optical means optical measurement. For example, in a case where a brain wave signal is measured at a time using an additional channel (the addition can be specified in the part 1208), the operator inputs EEG. The signals other than Optical can be separately processed during data analysis.

1207: A part for displaying a channel number of measurement.

1208: A part for specifying and displaying effectiveness (True) and ineffectiveness (False) of the channel number of the A/D converter. The specifying method is similar to the case of the part 1202. When False is selected in a channel, measurement in the specified channel is not performed.

1209: A window for inputting a character string or a number string in a position selected in the parts 1202 to 1208.

1210: A part for changing the dynamic range of the A/D converter. It become effective when the part 1204 is selected.

1211: A part for changing a gain of the lock-in amplifier. It become effective when the part 1203 is selected.

1212: A part for switching True and False in the columns 1202 and 1208.

1213: A part for selecting a displayed measurement mode. The word Each means that displayed tables are displayed by a plurality of tables for each wavelength, and the word All means that all the measuring channels are displayed by one table.

1214: A button for completing setting.

1215: A button for canceling setting.

According to the window of FIG. 12, checking and setting change can be easily performed because the monitor of the measurement conditions (1203 to 1208) and the conditions of graph display (1202) are shown on the single window. Further, a signal of another measurement instrument (apparatus) can be acquired using this window. Furthermore, the window of FIG. 12 is only one window that the operator inputs used conditions by selecting necessity of measuring input signals.

In a sub-menu window of Option in the measurement window of FIG. 10, the following windows is displayed depending on which is selected. However, displays of Trigger Pulse and External Trigger to be selected are omitted in FIG. 13.

Figure 15:
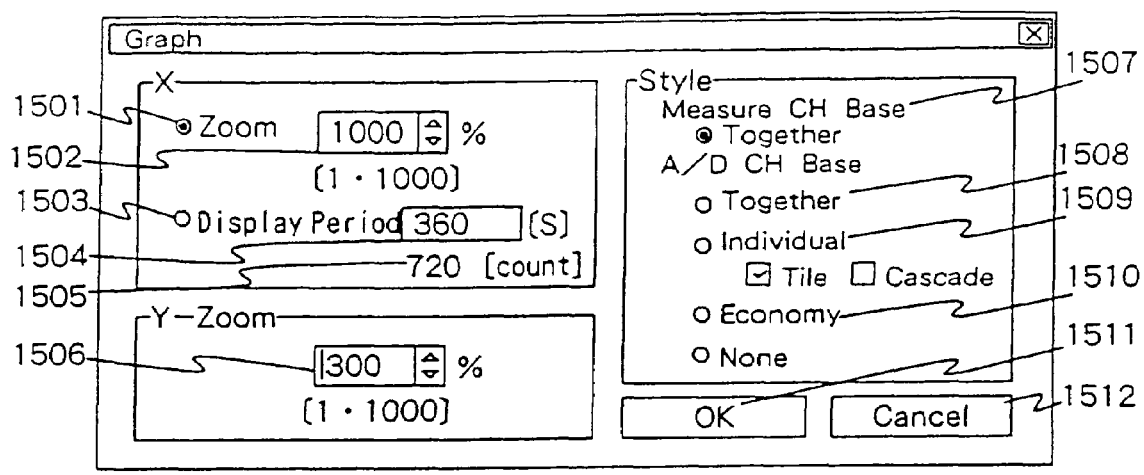
FIG. 15 is a view showing a window for inputting the display conditions of graph of FIG. 14 which is shown on the display portion.

Graph: A window for inputting the display conditions of graph of FIG. 14 (FIG. 15)

Figure 16:
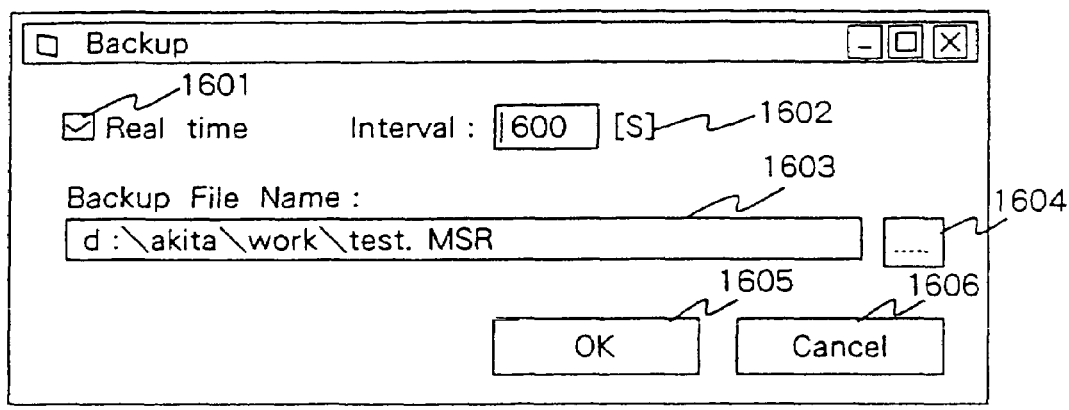
FIG. 16 is a view showing a window for inputting a file backup condition which is shown on the display portion.

Backup: A window for inputting a file backup condition (FIG. 16)

Figure 17:
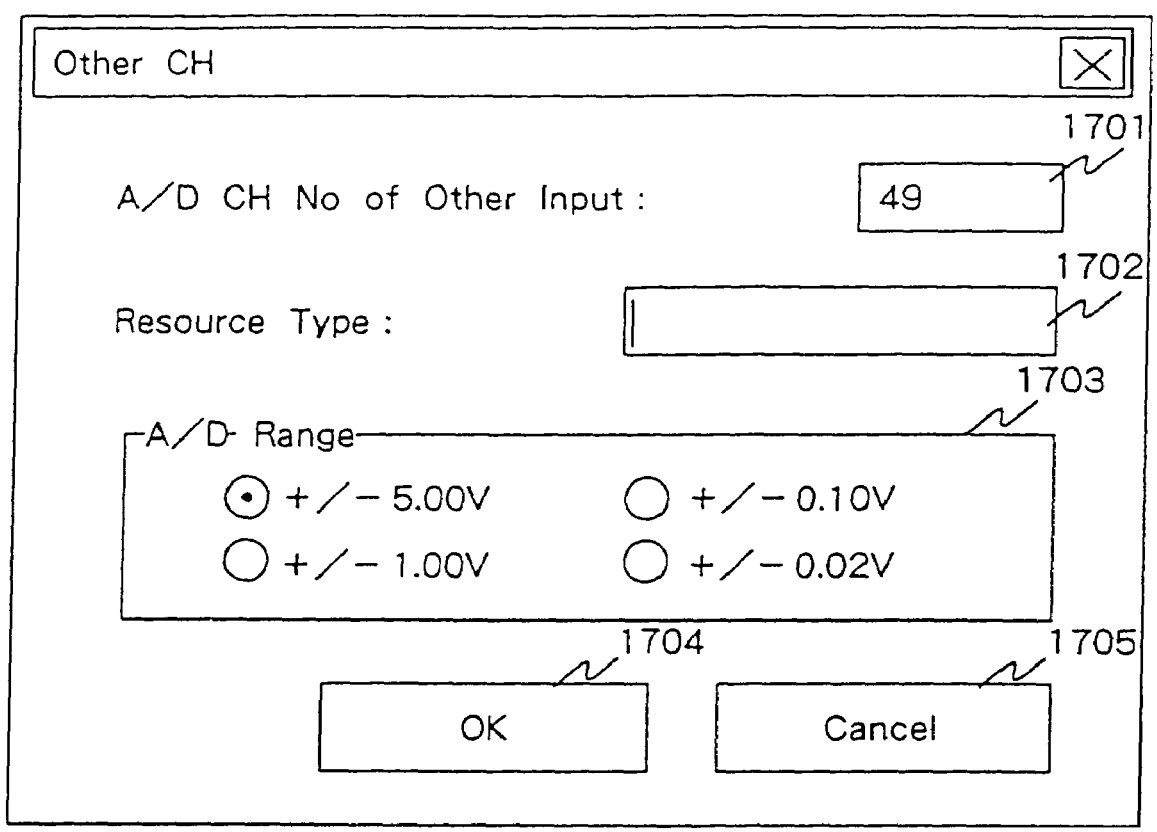
FIG. 17 is a view showing a window for input setting of the other measurement equipment output signal which is shown on the display portion.

Other CH: A window for input setting of the other measurement equipment output signal (FIG. 17)

Figure 18:
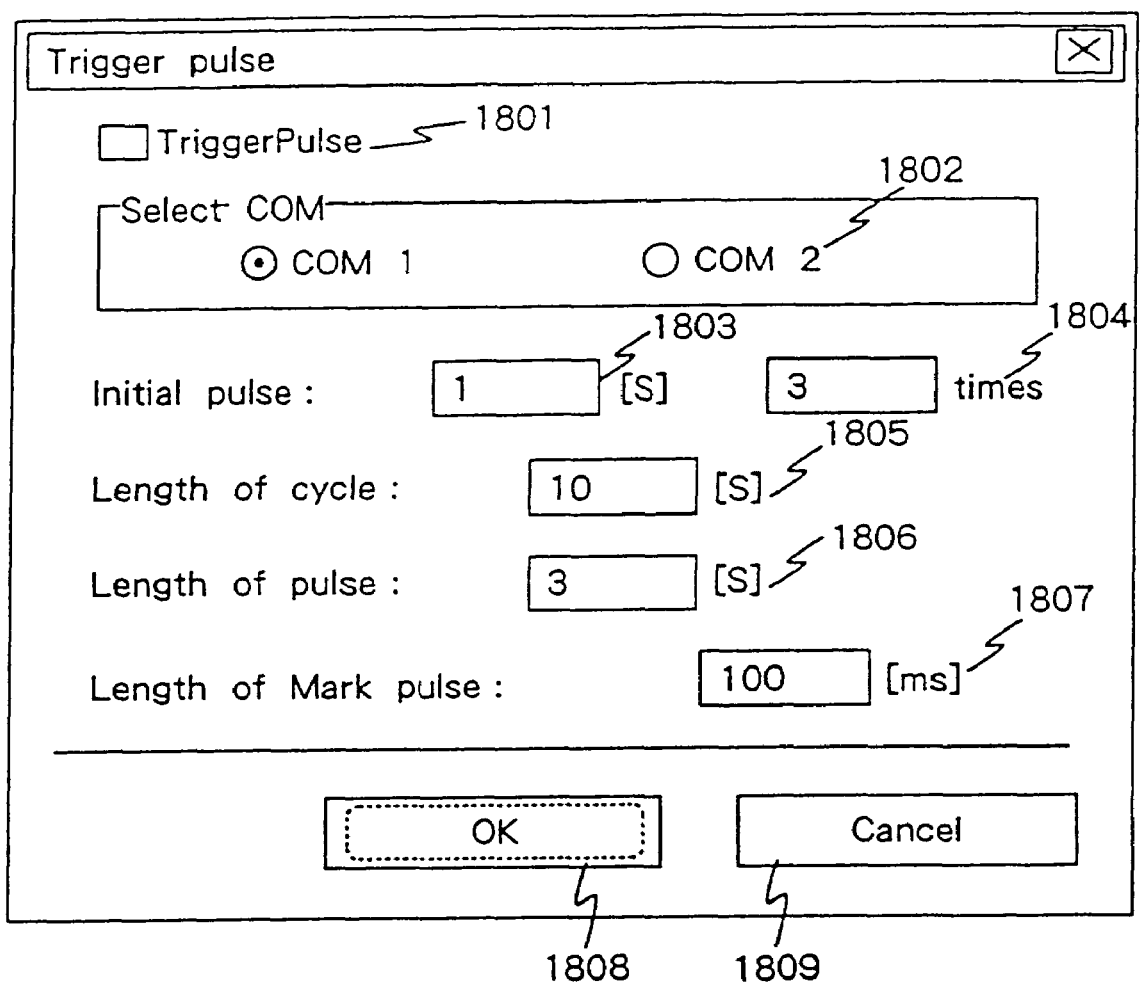
FIG. 18 is a view showing a window for setting a rectangular wave output signal which is shown in the display portion.

Trigger Pulse: A window for setting a rectangular wave output signal (FIG. 18)

Figure 20:
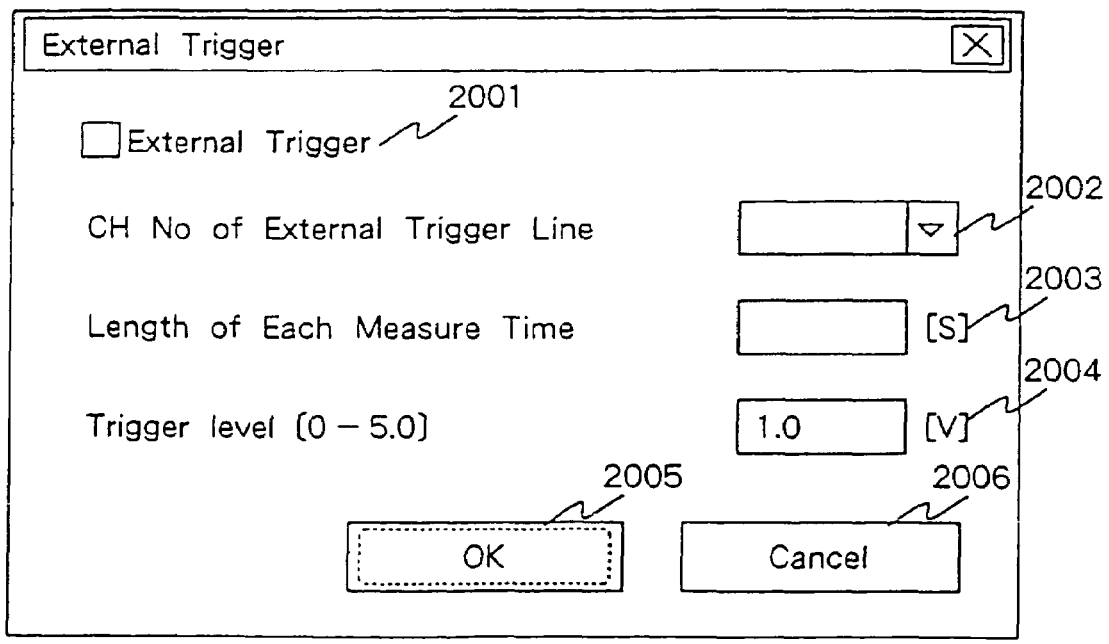
FIG. 20 is a view showing a window for setting an external input trigger synchronous measurement condition which is shown on the display portion.

External Trigger: A window for setting an external input trigger synchronous measurement condition (FIG. 20)

Figure 21:
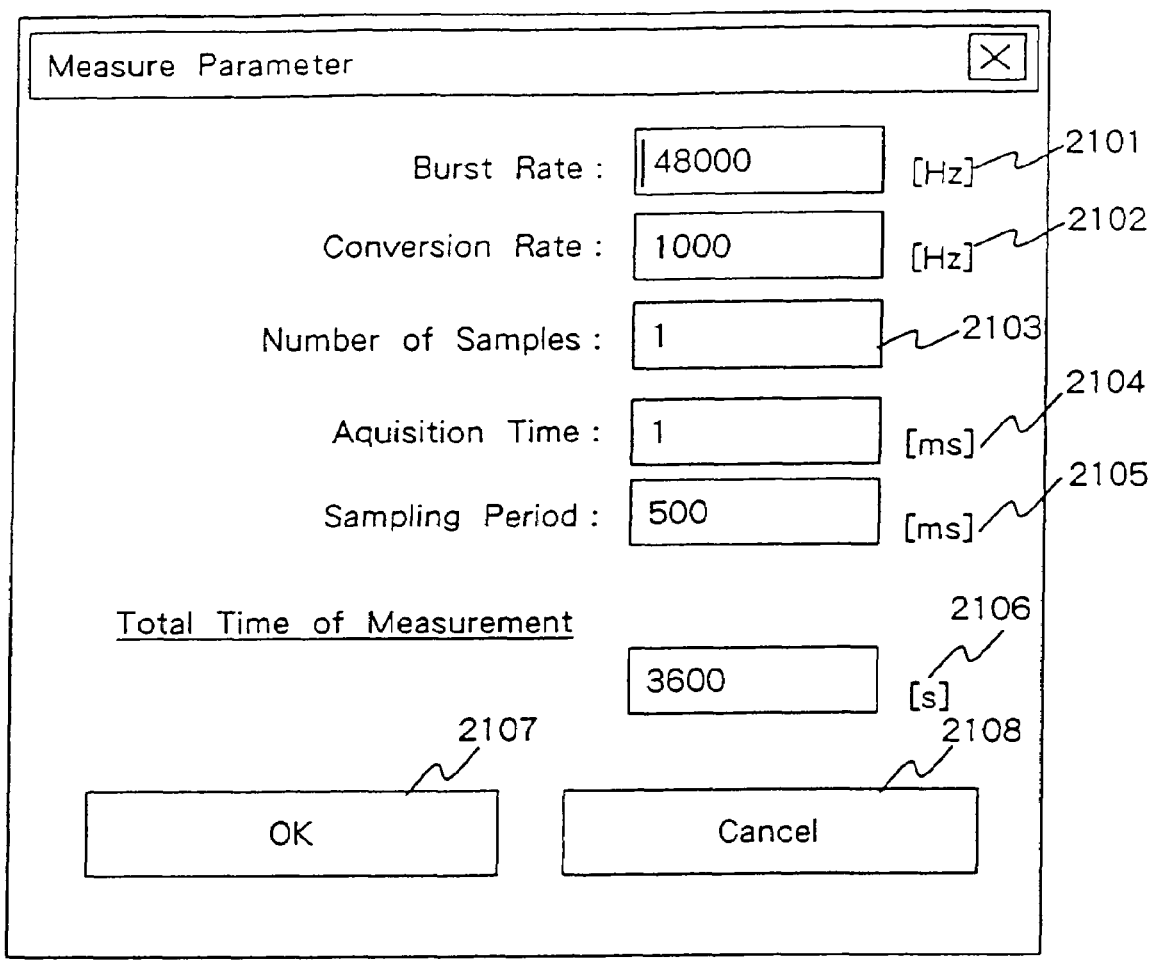
FIG. 21 is a view showing a window for setting a measured data acquiring condition which is shown on the display portion.

Measurement Parameter: A window for setting a measured data acquiring condition (FIG. 21)

Figure 22:
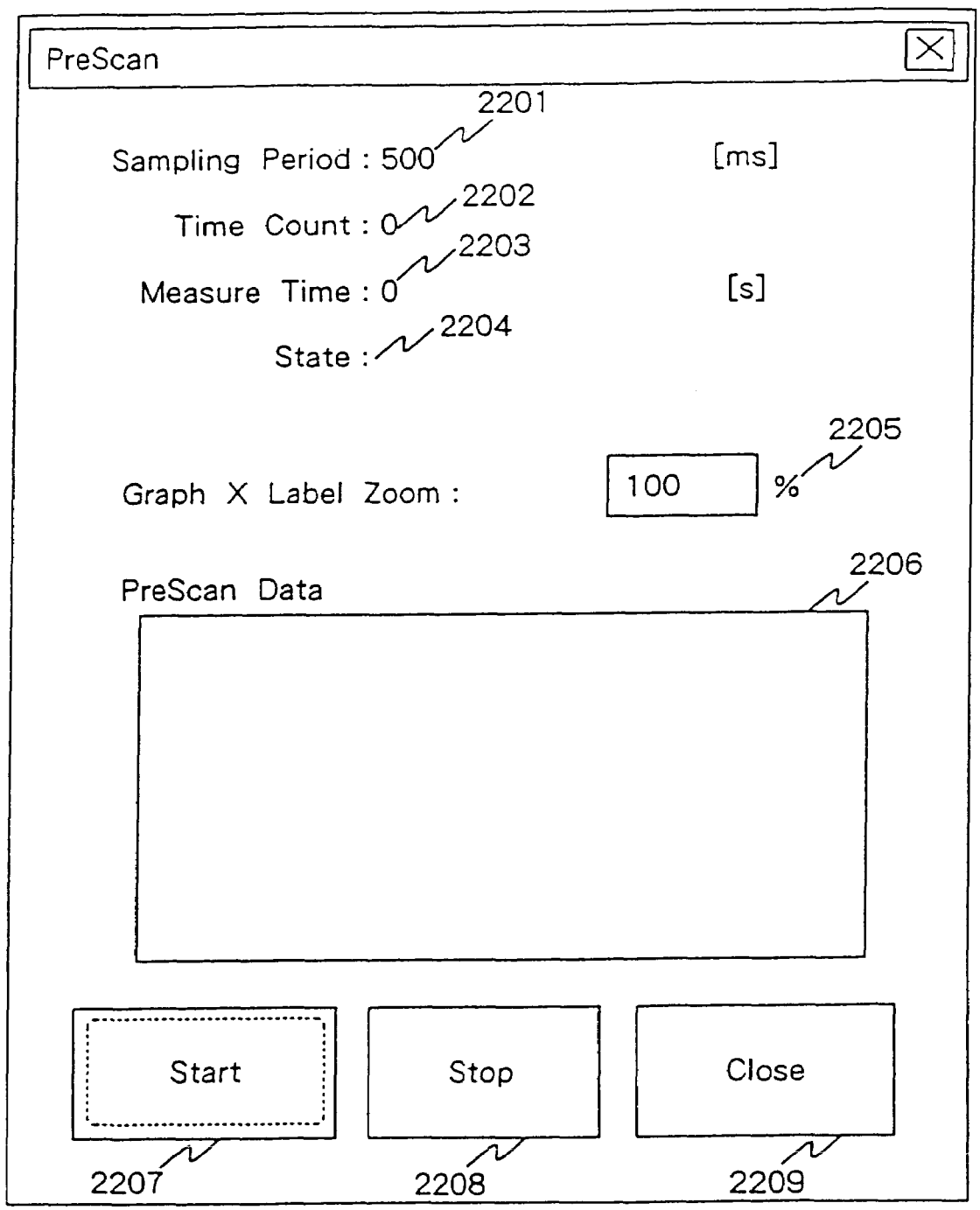
FIG. 22 is a view showing a window for checking a measured signal which is shown on the display portion.

Prescan: A window for checking a measured signal (FIG. 22)

Position: A window for displaying measured positions (FIG. 6) (returning to the step S6)

In regard to FIGS. 15 to 18 and 20 to 22, meaning and function of each part are as follows.

FIG. 15 (the window for inputting the display conditions of graph of FIG. 14) (S12)

1) A range of the X-axis is input. In order to input the range, there are two input methods, that is, one is a method of inputting a magnification performed in 1501, and the other is a method of inputting a displayed time performed in 1503.

1501: A button for selecting a display magnification inputting of the X-axis of graph.

1502: A part for inputting a display magnification of the X-axis of graph by a percentage. For example, in a case where the time period of 3600 seconds is displayed when the magnification is 100%, the displayed time period becomes within a range of 360 seconds if the magnification is changed to 1000% In this case, when the time exceeds 360 seconds, the window is scrolled to the left-hand side. In detail, assuming data of 362 seconds is acquired, the displayed range of the X-axis of the graph of FIG. 14 is from 2 seconds to 362 seconds.

1503: A button for selecting the displayed time inputting of the X-axis of the graph. When this button is selected, the button 1501 is automatically changed to not selected. The button 1501 and the button are mutually exclusive.

1504: A part for inputting a displayed time period of the X-axis of the graph.

1505: A part for displaying number of data kinds acquired within a displayed time period specified in the part 1504.

2) A range of the Y-axis is input.

1506: A part for selecting a display magnification inputting of the Y-axis of graph. The way of thinking is similar to that of the case of selecting a display magnification inputting of the X-axis of graph.

3) The format of graph display of FIG. 14 is selected.

1507: A button for selecting displaying all the channels (all the channels selected to display in FIG. 12) in order of the measured channel. When this button is selected, the windows shown in FIG. 14, number of which is equal to number of the wavelengths used in each measurement channel in number (two wavelengths in this embodiment), are displayed so as to overlap with each other. In that case, the first window shows signals of the first wavelength in order of the measured channel, and the second window shows signals of the second wavelength in order of the measured channel. If the setting is particularly not made, Together is selected.

1509: A button for displaying all the channels within a single window.

1509: A button for separately displaying within a window for each channel. Further, there are two kinds of display methods as follows.

Title: Graphs are displayed by arranging in a matrix-shape.

Cascade: Graphs are displayed by superposing on another.

1510: A button for displaying only one specified channel (the channel displayed in FIG. 12 can be selected).

1511: A part for forcing not displaying the graphs.

1512: A part for completing the setting. By completing the setting, the window display is returned to the window display of FIG. 10.

1513: A part for canceling. In the case of canceling, the window display is also returned to the window display of FIG. 10.

FIG. 16 (the window for inputting a file backup condition) (S13)

This window is for setting the condition of function of backup data during measurement at any time by assuming a case of a power outage during measuring or a case where a file specified by the window for forming a file of FIG. 8 is damaged due to some causes.

1601: A part for specifying whether or not backup is necessary.

1602: A part for inputting a backup time interval.

1603: A part for inputting a backup file name by full-pass.

1604: A part for referring to a directory and a file. The window for forming a file of FIG. 8 is displayed, and the specified file name is entered to Backup File Name area.

1605: A button for completing the setting. By completing the setting, the window display is returned to the window display of FIG. 10.

1606: A button for canceling. In the case of canceling, the window display is also returned to the window display of FIG. 10.

FIG. 17 (The window for input setting of the other measurement equipment output signal) (S14)

By this window, a signal output from another measurement instrument is acquired from data of a vacant A/D converter channel. A channel number of the A/D converter used at acquiring the data, a name of kind of the signal (EEG and so on) and a dynamic range of the A/D converter are selected.

1701: A part for displaying a channel number of a vacant A/D converter used for inputting. The vacant A/D converter having a least channel number is automatically allocated.

1702: A part for inputting a kind name of signal.

1703: A part for selecting a dynamic range of an A/D converter of another input.

1704: A button for completing the setting. By completing the setting, the window display is returned to the window display of FIG. 10.

1705: A button for canceling. In the case of canceling, the window display is also returned to the window display of FIG. 10.

FIG. 18 (The window for setting a rectangular wave output signal (S15)

A rectangular wave voltage signal is periodically output from the present optical measurement system. By inputting this signal into the other measurement instruments (a brain wave meter and so on), the measuring time can be strictly set in agreement between the instruments. The rectangular wave signal is output from, for example, a serial board of a personal computer.

Figure 19:
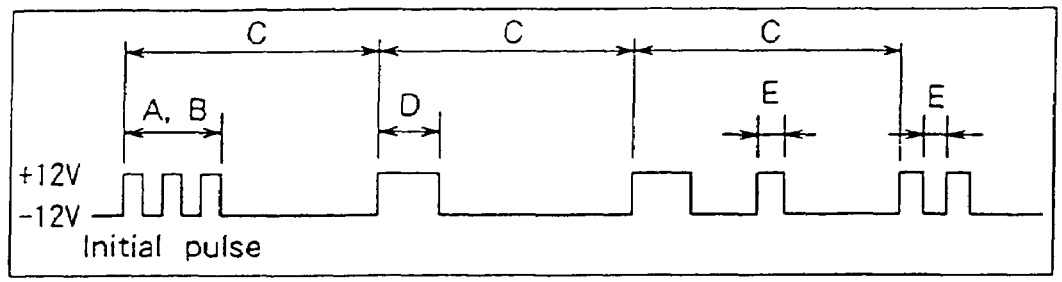
FIG. 19 is a chart showing the rectangular wave output signals of which the conditions are set in FIG. 18.

There are three kinds of the output rectangular wave signals, as shown in FIG. 19. The first kind is a rectangular wave signal which is output only at starting of measurement. The second kind is a rectangular wave signal which is periodically output until the measurement is completed. The third kind is a rectangular wave signal which is output in synchronism with pushing of the mark button of FIG. 10. The condition of these three kinds of rectangular wave signals can be set by the window of FIG. 18.

1801: Apart for selecting whether or not the rectangular wave output is necessary.

1802: A part for selecting a terminal to output the rectangular wave signal.

1803: A part for inputting a time width of the first kind of rectangular wave signal (refer to A of FIG. 19).

1804: A part for inputting number of repetitive times of the first kind of rectangular wave signal (refer to B of FIG. 19).

1805: A part for inputting number of repetitive times of the second kind of rectangular wave signal (refer to C of FIG. 19).

1806: A part for inputting a time width of the second kind of rectangular wave signal (refer to D of FIG. 19).

1807: A part for inputting a time width of the third kind of rectangular wave signal (refer to E of FIG. 19).

1808: A button for completing the setting. By completing the setting, the window display is returned to the window display of FIG. 10.

1809: A button for canceling. In the case of canceling, the window display is also returned to the window display of FIG. 10.

FIG. 20 (The window for setting an external input trigger synchronous measurement condition) (S16)

This window is a window which is used when measurement is performed in synchronism with a trigger signal from the external. By performing synchronous measurement, the time is completely in synchronism with the other measurement instrument and a stimulation apparatus.

2001: A part for specifying whether or not the external input trigger synchronous measurement is necessary.

2002: A part for inputting a channel number of the A/D converter used for the external input trigger signal.

2003: A part for inputting a measuring time to each trigger signal.

2004: A part for inputting a threshold value of a voltage value which is recognized as the trigger signal.

2005: A button for completing the setting. By completing the setting, the window display is returned to the window display of FIG. 10.

2006: A button for canceling. In the case of canceling, the window display is also returned to the window display of FIG. 10.

FIG. 21 (the window for setting a measured data acquiring condition) (S17)

By this window, a channel operating frequency of the A/D converter (Burst Rate), a sampling frequency per one channel of the A/D converter (Conversion Rate), an average number of adding times of acquired data (number of Samples), an adding time of acquired data (Acquisition Time), a data acquisition time interval (Sampling Period: the same as the part 1003 of FIG. 10) and a total measuring time can be set.

2101: A part for displaying and inputting Burst Rate.

2102: A part for displaying and inputting Conversion Rate.

2103: A part for displaying and inputting number of samples acquiring one sampling.

2104: A part for displaying a data acquisition time.

2105: A part for displaying and inputting a data acquisition time interval.

2106: A part for displaying and inputting a measurement time.

2107: A button for completing the setting. By completing the setting, the window display is returned to the window display of FIG. 10.

2108: A button for canceling. In the case of canceling, the window display is also returned to the window display of FIG. 10.

FIG. 22 (The window for checking a measured signal) (S18)

This window is used for that the operator checks the state of signals by performing pre-measurement in prior to starting the actual measurement, if necessary. A value of signal displayed in the graph is expressed by a voltage value.

2201: A part for displaying a data acquisition time interval.

2202: A part for displaying number of data acquisition times (number of sampling times).

2203: A part for displaying a measuring elapsing time.

2204: A part for displaying a measuring state (refer to FIG. 10).

2205: Apart for specifying a magnification of the X-axis of the graph (refer to FIG. 15).

2206: A part for displaying the result of pre-measurement by numerical values for each channel.

2207: A button for starting of checking output signals. When this button is pushed, the measured signals are displayed in a single window or a plurality of windows shown in FIG. 14 corresponding to the form of the graph set by the window shown in FIG. 15.

2208: A button for aborting measurement.

2209: A button for completing the pre-measurement. By pushing this button, the display window is returned to the 20 display window of FIG. 10.

By the embodiment described above, an operator, even if not skilled, can perform input work speedily and without error. Further, there are provided the option functions which can be set by an operator.

According to the present invention, it is possible to provide an optical measurement system and an optical measurement method which is suitable for optically measuring a body to be inspected and easily obtaining an image of a desired item based on information obtained by the measurement.

Further, according to the present invention, an operator, even if not skilled, can perform input work speedily and without error. Accordingly, the operator can perform the optical measurement operation even if he is not understand the operating manual very well.

Furthermore, according to the present invention, it is possible to understand a state of change in a body to be inspected, for example, an activation state of cerebral oxygen metabolism with high accuracy.

What is claimed is:

1. An optical measurement system comprising:
   a plurality of light sources for irradiating light on a biological body;
   a plurality of light detectors for detecting light which is irradiated from said light sources and propagate through said biological body;
   a computer for calculating the concentration of oxygenated hemoglobin and deoxygenated hemoglobin; and
   a display for displaying a calculated results of said computer; wherein said display displays a window for showing correspondence between a measuring channel of a plurality of measuring channels and a channel of an A/D converter of a plurality of channels of an A/D converter, where which measuring channels to use for measuring or which measuring channels to display is specified.

2. An optical measurement system according to claim 1, wherein
   said window has a part for changing a dynamic range of said A/D converter, or a part for changing a gain of a lock-in amplifier.

3. An optical measurement system according to claim 1, wherein
   said window has a part for selecting whether to acquire a signal of another measurement instrument.

* * * * *